(12) United States Patent
Placke et al.

(10) Patent No.: US 6,419,901 B2
(45) Date of Patent: *Jul. 16, 2002

(54) METHOD FOR TREATING NEOPLASMS BY INHALATION

(75) Inventors: Michael E. Placke, Columbus; Anthony R. Imondi, Westerville, both of OH (US)

(73) Assignee: Battelle Pulmonary Therapeutics, Columbus, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 09/875,677

(22) Filed: Jun. 6, 2001

Related U.S. Application Data

(63) Continuation of application No. 09/000,775, filed on Dec. 30, 1997.
(60) Provisional application No. 60/033,789, filed on Dec. 30, 1996.

(51) Int. Cl.[7] .............................. A61L 9/04; A61K 9/14
(52) U.S. Cl. ........................ 424/45; 424/489; 424/43; 424/46
(58) Field of Search .................................. 474/422, 435, 474/489, 485, 43, 45, 46; 514/34, 283, 449

(56) References Cited

U.S. PATENT DOCUMENTS

| 4,246,399 A | 1/1981 | Higuchi et al. |
|---|---|---|
| 4,560,774 A | 12/1985 | Pettit et al. |
| 4,571,334 A | 2/1986 | Yoshida et al. |
| 4,649,911 A | 3/1987 | Knight et al. |
| 4,675,311 A | 6/1987 | Gatti et al. |
| 4,814,161 A | 3/1989 | Jinks et al. |
| 4,818,752 A | 4/1989 | Williams et al. |
| 4,826,817 A | 5/1989 | Brown et al. |
| 4,946,831 A | 8/1990 | Gatti et al. |
| 4,963,367 A | 10/1990 | Ecanow |
| 4,975,421 A | 12/1990 | Williams et al. |
| 5,049,388 A | 9/1991 | Knight et al. |
| 5,091,372 A | 2/1992 | Gatti et al. |
| 5,091,373 A | 2/1992 | Gatti et al. |
| 5,115,971 A | 5/1992 | Greenspan et al. |
| 5,124,317 A | 6/1992 | Gatti et al. |
| 5,124,318 A | 6/1992 | Gatti et al. |
| 5,171,737 A | 12/1992 | Weiner et al. |
| 5,268,164 A | 12/1993 | Kozarich et al. |
| 5,273,965 A | 12/1993 | Kensil et al. |
| 5,283,383 A | 2/1994 | Boyd et al. |
| 5,301,664 A | 4/1994 | Sievers et al. |
| 5,348,946 A | 9/1994 | Attardo et al. |
| 5,438,072 A | 8/1995 | Bobee et al. |
| 5,439,686 A | 8/1995 | Desai et al. |
| 5,511,726 A | 4/1996 | Greenspan et al. |
| 5,531,219 A | 7/1996 | Rosenberg |

(List continued on next page.)

FOREIGN PATENT DOCUMENTS

| EP | 0 645 145 A2 | 3/1995 |
|---|---|---|
| EP | 0 525 960 B1 | 3/1996 |
| EP | 0 709 090 A2 | 5/1996 |

(List continued on next page.)

OTHER PUBLICATIONS

U.S. application No. 09/504,047, Roosdorp et al., filed Apr. 3, 1990.

(List continued on next page.)

Primary Examiner—Thurman K. Page
Assistant Examiner—Rachel M. Bennett
(74) Attorney, Agent, or Firm—Patricia A. Coburn; Klaus Wiesmann

(57) ABSTRACT

A formulation, method, and apparatus for treating neoplasms such as cancer by administering a pharmaceutically effective amount of highly toxic composition by inhalation, wherein the composition is a non-encapsulated antineoplastic drug.

24 Claims, 6 Drawing Sheets

U.S. PATENT DOCUMENTS

| | | |
|---|---|---|
| 5,543,152 A | 8/1996 | Webb et al. |
| 5,561,122 A | 10/1996 | Pettit |
| 5,565,478 A | 10/1996 | Kohn et al. |
| 5,591,715 A | 1/1997 | Coon et al. |
| 5,591,737 A | 1/1997 | Doherty et al. |
| 5,593,970 A | 1/1997 | Attardo et al. |
| 5,602,112 A | 2/1997 | Rubinfeld |
| 5,605,674 A | 2/1997 | Purewal et al. |
| 5,606,037 A | 2/1997 | Attardo et al. |
| 5,607,691 A | 3/1997 | Hale et al. |
| 5,612,474 A | 3/1997 | Patel |
| 5,616,334 A | 4/1997 | Janoff et al. |
| 5,627,270 A | 5/1997 | Kahne et al. |
| 5,641,774 A | 6/1997 | Varney et al. |
| 5,645,988 A | 7/1997 | Vande Woude et al. |
| 5,655,523 A | 8/1997 | Hodson et al. |
| 5,665,382 A | 9/1997 | Grinstaff et al. |
| 5,676,930 A | 10/1997 | Jager et al. |
| 5,681,545 A | 10/1997 | Purewal et al. |
| 5,709,202 A | 1/1998 | Lloyd et al. |
| 5,855,913 A | 1/1999 | Hanes et al. |

FOREIGN PATENT DOCUMENTS

| | | |
|---|---|---|
| EP | 0 486 959 B1 | 8/1996 |
| GB | 2 178 311 A | 2/1987 |
| WO | WO 91/08760 | 6/1991 |
| WO | WO 92/16192 | 10/1992 |
| WO | WO 93/17665 | 9/1993 |
| WO | WO 93/21938 | 11/1993 |
| WO | WO 94/10175 | 5/1994 |
| WO | WO 94/12031 | 6/1994 |

OTHER PUBLICATIONS

International Search Report, PCT/US97/24289, Mar. 3, 1999.

International Preliminary Examining Authority—Written Opinion, PCT/US97/24289 (now WO 98/29110), Mar. 28, 1999.

Abra, R.M. et al; Delivery of Therapeutic Doses of Doxorubicin to the Mouse Lung Using Lung–Accumulating Liposomes Proves Unsccessful; Cancer Chemother. Pharmacol.; vol. 11; 1983; pp. 98–101.

Bertelli, G.; Prevention and Management of Extravasation of Cyto–toxic Drugs; Drug Safety; vol. 12; No. 4; 1995; pp. 245–255.

Bicher, A. et al; Infusion Site Soft–Tissue Injury After Paclitaxel Administration; Cancer; vol. 76; No. 1; Jul. 1, 1995; pp. 116–120.

Boyle, D.M. et al; Vesicant Extravasation: Myths and Realities; Oncol. Nurs. Forum; vol. 22; No. 1; Jan. 1995; pp. 57–67.

Budd, G.T. et al; Clinical Effects of Amifostine (Ethyl$^{(R)}$) in Patients Treated With Carboplating; European Journal of Cancer; vol. 32A; Suppl. 4; 1996; pp. S43–S45.

Cuddihy, R.G. et al; Respiratory Tract Deposition of Inhaled Polydisperse Aerosols in Beagle Dogs; Aerosol Science; vol. 4; 1973; pp. 35–45.

Dorr, R.T.; Author Reply to G. Bertelli et al, Correspondence Section,re Skin Ulceration Potential of Paclitaxel in a Mouse Skin Model in Vivo; Cancer; vol. 79; No. 11; Jun. 1, 1997; pp. 2268–2269..

Dorr, R.T. et al; Lack of Experimental Vesicant Activity for the Anticancer Agents Cisplatin, Melphalan, and Mitoxantrone; Cancer Chemother. Pharmacol.; vol. 16; 1986; pp. 91–94.

Herman, E.H. et al; Morphologic and Morphometric Evaluation of the Effect of ICRF–187 on Bleomycin–Induced Pulmonary Toxicity; Toxicology; vol. 98; 1995; pp. 163–175.

Juliano, R.L. et al; Controlled Delivery of an Antitumor Drug: Localized Action of Lipsome Encapsulated . . . ; Journal of Pharmacology and Experimental Therapeutics; vol. 214; No. 2; 1980; pp. 381–387.

Khanna, C. et al; Aerosol Delivery of Interleukin–2 Liposomes is Nontoxic and Effective: Murine and Canine Studies; Proc. Annual Mtg. of Amer. Assoc. of Cancer Res.; vol. 35; 1994; A2470 (meeting abstract).

Khanna, C. et al; Interleukin–2 Liposome Inhalation Therapy is Safe and Effective for Dogs with Spontaneous Pulmonary Metastases; Cancer; vol. 79; No. 7; Apr. 1, 1997; pp. 1409–1421.

Kinnula, V. et al; Effect of Inhaled Natural Interferon–Alpha on Diffuse Bronchioalveolar Carcinoma; Eur. J. Cancer; vol. 26; No. 6; 1990; pp. 740–741.

Kinnula, V. et al; Pharmacokinetics and Toxicity of Inhaled Human Interferon–$\alpha$ in Patients with Lung Cancer; Journal of Interferon Research; vol. 9; 1989; pp. 419–423.

Knight, J.A.; Diseases Related to Oxygen–Derived Free Radicals; Annals of Clinical and Laboratory Science; vol. 25; No. 2; Mar.–Apr. 1995; pp. 111–121.

Kinoshita, A.; Investigation of Cisplatin Inhalation Chemotherapy Effects of Mice After Air Passage Implantation of FM3A Cells; J. Jpn. Soc. Cancer Ther.; vol. 28; No. 4; 1993; pp. 705–715.

Koyama, S. et al; Experimental and Clinical Studies of Nebulization Chemotherapy in the Treatment of Lung Cancer; J. Jpn. Soc. Cancer Ther.; vol. 23; No. 3; Mar. 1988; pp. 759–770 (Japanese w/English abstract.

Lewis, C.; A Review of the Use of Chemprotectants in Cancer Chemotherapy; Drug Safety; vol. 11; No. 3; 1994; pp. 153–162.

Li, C. et al; Synthesis and Evaluation of PEG–Paclitaxel Conjugate as a Water Soluble Paclitaxel Prodrug; Scientific Proceedings Annual meeting of the Am. Assoc. for Cancer Research; vol. 37; 1996; p. 376 (Abstract only).

McCullough, H.N. et al; Organ–Selective Action of an Antitumor Drug: Pharmacologic Studies of Liposome–Encapsulated Beta–Cytosine Arabinoside Administered via the Respiratory System of the Rat; JNCI; vol. 63; No. 3; Sep. 1979; pp. 727–730.

Myers, C.E. et al; Adriamycin: The Role of Lipid Peroxidation in Cardiac Toxicity and Tumor Response; Science; vol. 197; 1977; pp. 165–167.

Newman, S.P.; Therapeutic Aerosols (Chapter 9); in *Aerosols and the Lung;* Clarke and Davis (eds.); Butterworths, London, England; 1984; pp. 197–224.

Okuyama, S. et al; Reinforcing Aerosol Cisplatin for Radiotherapy of Laryngeal Cancer; Tohoku J. Exp. Med.; vol. 169; 1993; pp. 253–255.

Physicians' Desk Reference; 51st Edition, Published by Medical Economics Company; Montvale NJ 07645–1742; 1997; pp. 697–699, 1666–1667, 531–533, 539–541, 2096–2099, 2060–2064, 1752–1754, 1322–1327, 712–713, 723–727, 1537–1540, 1521–1523.

Rudolph, R. et al; Eitology and Treatment of Chemotherapeutic Agent Extravasation Injuries: A Review; Journal of Clinical Oncology; vol. 5; No. 7; 1987; pp. 1116–1126.

Shevchenko, I.T. et al; Inhalation of Chemical Substances and Oxygen in Radiotherapy of Bronchial Cancer; Neoplasma; vol. 15; No. 4; 1968; pp. 419–426.

Sugawa, I.; A Study on Transairway Carcinostatic Dose for Lung Metastases; Ochanomizu Med. J.; vol. 18; No. 3; 1970; pp. 103–114.

Task Group on Lung Dynamics, Bates, D.V. et al; Deposition and Retention Models for Internal Dosimetry of the Human Respiratory Tract; Health Physics; Pergamon Press; vol. 12; 1996; pp. 173–207.

Tatsumura, T. et al; Further Evaluation of the Efficacy of Nebulization Chemotherapy in the Treatment of Lung Cancer; Chest; vol. 106; No. 2 Supplement; 1994; pp. 70–79.

Tatsumura, T. et al; Further Study of Nebulisation Chemotherapy, a New Chemotherapeutic Method in the Treatment of Lund Carcinomas: Fundamental and Clinical; Br. J. Cancer; vol. 68; 1993; pp. 1146–1149.

Tatsumura, T. et al; Nebulization Chemotherapy, a New Chemotherapeutic Method for the Treatment of Lung Cancer; Proc. Am. Soc. Oncol.; vol. 9; No. 961; 1990; pp. 248.

Medline Abstract 83269156; New Chemotherapeutic Method for the Treatment of Tracheal and Bronchial Cancers—Nebulization Chemo–Therapy; National Library of Medicine; Bethesda, MD:1983, Jun., 29(7):765–7

Tatsumura, T. et al; The Usefulness of the Nebulization Chemo–therapy in the Treatment of Lung Cancer; Jap. Chest (best guess by translator); vol. 54; No. 8; 1995; pp. 631–638.

Vail, D.M. et al; Liposome–Encapsulated Muramyl Tripeptide Phosphatidylethanolamine Adjuvant Immunotherapy . . . ; Clinical Cancer Research; vol. 1; Oct. 1995; pp. 1165–1170.

Van Zandwijk, N. et al; Aerosol Application of Interferon–Alpha in the Treatment of Bronchioloalveolar Carcinoma; Eur. J. Cancer; vol. 26; No. 6; 1990; pp. 738–740.

Gutierrez, Andres A. et al., Gene Therapy for Cancer; The Lancet; vol. 339; Mar. 21, 1992; pp. 715–721.

Huland, Edith et al.; Inhaled Interleukin–2 in Combination With Low Dose Systemic Interleukin–2 and Interferon . . . ; J. Cancer Res. Clin. Oncol. vol. 120; 1994; pp. 221–228.

Koyama, Shinji et al.; Study on Trans–Oral Administration of 5–Fluorouracil in the Treatment of Lung Cancer; Journal of the Japanese Society of Cancer Therapy; vol. 23; No. 3; Mar. 1988; pp. 759–770.

Lorenz, Joachim et al.; Phase I Trial of Inhaled Natural Interleukin 2 for the Treatment of Pulmonary Malignancy . . . ; Clinical Cancer Research; vol. 2; Jul. 1996; pp. 1115–1122.

Mazue, G. et al.; Anthracyclines: A Review of General and Special Toxicity Studies; International Journal of Oncology; vol. 7; 1995; pp. 713–726.

Mujoo, Kalpana et al.; Adenoviral–Mediated p53 Tumor Suppressor Gene Therapy of Human Ovarian Carcinoma; Oncogene; vol. 12; 1996; pp. 1617–1623.

Murphy, Gerald P. et al. American Cancer Society Textbook of Clinical Oncology. Second Edition. pp. 101–110, Apr. 1995.

Pollera, C.F. et al.; High Dose–Intense Chemotherapy Alone or in Combination with Interleukin–2 for Small Cell Lung Cancer; A Pilot Study; Cancer Investigation; vol. 12; No. 6; 1994; pp. 574–587.

Sonnenveld, Erick J.A. et al.; Systemic Toxicity After Isolated Limp Perfusion With Melphalan for Melanoma; European Journal of Surgical Oncology; vol. 22; 1996; pp. 521–527.

Tan, Yuying et al.; IL–2 Gene Therapy of Advanced Lung Cancer Patients; Anticancer Research; vol. 16; 1996; pp. 1993–1998.

Tatsumura, T. et al.; New Chemotherapeutic Method for the Treatment of Trachael and Bronchial Cancer—Nebulization Chemotherapy; Gan no Rinsho; vol. 29; No. 7; Jun. 1983; pp. 766–770.

Vrouenraets, B.C. et al.; Thirty–Five Years of Isolated Limb Perfusion for Melanoma: Indications and Results; British Journal of Surgery; vol. 83; 1996; pp. 1319–1328.

Wolgemuth, L. et al.; Doxorubicin Extravasation Ulceration: Animal Model Development and Testing of Potential Antidotes; Proc. Am. Assoc. Cancer Res. (US); vol. 23; 1982; p. 673; Abstract only.

METHOD FOR TREATING NEOPLASMS BY INHALATION

This application is a continuation of 09/000,775 filed Dec. 30, 1997 which claims the benefit of U.S. Provisional Application No. 60/033,789 filed on Dec. 30, 1996.

FIELD OF THE INVENTION

The invention deals with formulations and methods useful for treating neoplasms, particularly neoplasms of the respiratory tract (e.g. lung cancer and cancers of the head and neck), by pulmonary administration of highly toxic or vesicating anticancer drugs. Additionally, several new formulations and methods for treating neoplasms using antineoplastic drugs that are nonvesicants are also disclosed.

BACKGROUND OF THE INVENTION

Cancer is one of the leading causes of death worldwide. Lung cancer in particular, is among the top 3 most prevalent cancers and has a very poor survival rate (about 13% five-year survival rate). Despite the availability of many cancer drugs it has been difficult and, in the case of some cancer types, almost impossible to improve cure rates or survival. There are many reasons for this lack of success but one reason is the inability to deliver adequate amounts of the drugs to the tumor without causing debilitating and life-threatening toxicities in the patient. Indeed, most chemotherapeutic drugs used to treat cancer are highly toxic to both normal and tumor tissues.

It is customary in the treatment of cancer to administer the drugs by the intravenous route, which exposes the entire body to the drug. Doses are selected that destroy tumor cells, but these doses also destroy normal cells. As a result, the patient usually experiences severe toxic side effects. For example, severe myelosuppression may result which compromises the ability of the patient to resist infection and allows spread of the tumor. There are other life-threatening effects such as hepatotoxicity, renal toxicity, pulmonary toxicity, cardiotoxicity, neurotoxicity, and gastrointestinal toxicity caused by anticancer drugs. The anticancer drugs also cause other effects such as alopecia, stomatitis, and cystitis that may not be life threatening, but are serious enough to affect a patient's quality of life. Moreover, it is important to note that these toxicities are not associated to the same extent with all anticancer drugs but are all due to systemic delivery of the drug.

Although myelosuppression is commonly associated with most anticancer drugs, because of differences in the mechanisms by which the various anticancer drugs act or in the ways they are distributed in the body, metabolized and excreted from the body, each drug presents a somewhat different toxicity profile, both quantitatively and qualitatively. For example, anthracyclines such as doxorubicin, epirubicin and idarubicin are known to cause severe cardiotoxicity. Doxorubicin, additionally, is known to cause severe progressive necrosis of tissues when extravasated. Cisplatin therapy is known to cause renal toxicity; vincristine causes neurotoxicity, bleomycin and mitomycin cause pulmonary toxicity, cyclophosphamide causes cystitis; and 5-fluorouracil causes cerebral disjunction (see Cancer Chemotherapy: Principles and Practice, B A Shabner and J. M. Collings, eds. J. B. Lippincott Co., Philadelphia, 1990).

The differences in mechanisms of action and pharmacokinetic properties determine, in part, the efficacy of the various anticancer drugs against different tumor types, which exhibit various biological behaviors.

Some attempts have been made to deliver anticancer drugs directly to the tumor or to the region of the tumor to minimize exposure of normal tissues to the drug. This regional therapy, for example has been used to treat liver cancer by delivering drugs directly into the hepatic artery so that the full dose goes to the liver while reducing the amount that goes to the rest of the body. For the treatment of urinary bladder cancer, anticancer drugs are instilled directly into the bladder through the urethra, allowed to remain in contact with the tumor for a period of time and then voided. Other examples of regional therapy include the delivery of anticancer drugs into the peritoneal cavity to treat cancer that has developed in or metastasized to this location. Other methods of targeting anticancer drugs involve the attachment of the drugs to antibodies that seek out and deliver the drug directly to the cancer cells.

In 1968 Shevchenko, I. T., (Neoplasma 15, 4, 1968) pp.419–426 reported on the treatment of advanced bronchial cancer using a combination of inhalation of chemotherapeutic agents, radiotherapy, and oxygen inhalation. The reported chemotherapeutic agents were benzotaph, thiophosphamid, cyclophosphan and endoxan that were applied as an aerosol by means of an inhaler. For 58 treated patients the combination of three treatments showed tumor disappearance in 8 cases while in 6 the size of the tumor diminished considerably. The study did not include a control group.

In 1970, Sugawa, I. (Ochanoizu Med. J.; Vol. 18; No.3; (1970), pp.103–114, reported on tests using mitomycin-C in the treatment of metastatic lung cancer. One of four patients treated reportedly showed some improvement. Inhalation of mitomycin-C also appeared to reduce tumor growth in IV-inoculated tumors in rabbits; results appeared to be more inconclusive in rats. Tests were conducted to determine the toxic effects to the respiratory tract following intrabronchial infusions of several drugs. The drugs were given to healthy animals and included: thiotepa (rats), Toyomycin (chromomycin A3) (rats,), endoxan (cyclophosphamide) (rats and rabbits), 5-fluorourcil (rats and rabbits), mitomycin-C (rats, rabbits, and dogs). The results of these tests showed that: 5-FU and cyclophosphamide resulted in only mild inflammation; thiotepa produced bronchial obstruction; chromomycin A3 and mitomycin-C produced the most severe results. Toxic effects of mitomycin-C and chromomycin A3 were studied in rabbits and dogs.

In 1983, Tatsumura et al (Jap. J. Cancer Cln., Vol. 29, pp. 765–770) reported that the anticancer drug, fluorouracil (5-FU, MW=130) was effective for the treatment of lung cancer in a small group of human patients when administered directly to the lung by aerosolization. They referred to this as nebulization chemotherapy. It was also noted by Tatsamura et al (1993) (Br. J. Cancer, Vol. 68(6): pp.1146–1149) that the 5-FU did not cause toxicity to the lung. This finding was not totally unexpected because 5-FU has a very low molecular weight and does not bind tightly to proteins. Therefore, it passes through the lung rapidly lessening the opportunity to cause local toxicity. Moreover 5-FU is considered to be one of the least toxic anticancer drugs when applied directly to tissue. Indeed, 5-FU is used as a topical drug for the treatment of actinic keratosis for which it is applied liberally, twice daily, to lesions on the face. This therapy may continue for up to four weeks. Also, because 5-FU is poorly absorbed from the gastrointestinal tract, there is little concern about the amount of drug that may be inadvertently swallowed and gain access to the blood stream from the gut. It is well known that a large percentage of aerosolized drug intended for the lung is swallowed.

Another report includes the use of β-cytosine arabinoside (Ara-C, cytarabine, MW=243) administered via intratracheal delivery to the respiratory system of rats. Liposome encapsulated and free Ara-C were instilled intratracheally to the rats as a bolus. The encapsulated Ara-C persisted for a long time in the lung while the free Ara-C which is not highly protein bound was rapidly cleared from the lung. The free Ara-C rapidly diffused across the lung mucosa and entered the systemic circulation. The paper suggests that liposome encapsulation of drugs may be a way to produce local pharmacologic effect within the lung without producing adverse side effects in other tissues. However, bolus administration results in multifocal concentrated pockets of drug. See the articles by H. N. MacCullough et al, JNCI, Vol. 63, No. 3, September, pp.727–731 (1979) and R. L. Juliano et al, J. Ph. & Exp. Ther., Vol. 214, No.2, pp.381–387 (1980).

An additional report includes the use of cisplatin (MW=300) for inhalation chemotherapy in mice that had been implanted with FM3A cells (murine mammary tumor cells) in the air passages. The cisplatin exposed inhalation group were reported to have statistically smaller lung tumor sizes and survived longer than the untreated control group. See A. Kinoshita, "Investigation of Cisplatin Inhalation Chemotherapy Effects on Mice after Air Passage Implantation of FM3A Cells", J. Jap. Soc. Cancer Ther. 28(4): pp. 705–715 (1993).

In U.S. Pat. No. 5,531,219 to Rosenberg, the patent disclosure suggests the use of doxorubicin, 5-FU, vinblastine sulfate, or methotrexate in combination with pulmonary infused liquid fluorocarbons. The patient is suggested to be positioned so that the tumor affected area is at a gravitational low point so that liquid perfluorocarbon having relatively low vapor pressure will pool selectively around the area with the drug then perfused in the pool of liquid perfluorocarbon. The present invention avoids the problems with positioning of the patient and further does not require the liquid fluorocarbons used by Rosenberg.

In U.S. Pat. No. 5,439,686 to Desai et al there are disclosed compositions where a pharmaceutically active agent is enclosed within a polymeric shell for administration to a patient. One of the routes of administration listed as possible for the compositions of the invention is inhalational. Among the listed pharmaceutically active agents potentially useful in the invention are anticancer agents such as paclitaxel and doxorubicin. No tests using the inhalational rout of administration appear to have been made.

Although several antineoplastic drugs have been administered to animals and to humans, for treatment of tumors in the lungs and respiratory system, the differences in the mechanism of action, and toxicity profiles among the broad classes of anticancer drugs, and the heretofore known characterizations have made it impossible to predict whether a particular anticancer drug will be efficacious or toxic based upon previous inhalation results with a different drug of a different type. Further, previous reports used very imprecise means of delivering drugs and were not consistent in delivering measured doses of drugs in an evenly distributed manner to the entire respiratory tract. The present invention provides means for predicting and selecting drugs including the highly toxic chemotherapeutic compounds, amenable for inhalation therapy of neoplastic disease and methods for actually distributing specific measured doses to pre-selected regions of the respiratory tract.

It has now been demonstrated by the applicants that anticancer cytotoxic drugs of multiple classes such as anthracyclines (doxorubicin), antimicrotubule agents such as the vinca alkaloids (vincristine), and taxanes such as paclitaxel can be given directly by inhalation without causing severe toxicity to the lung or other body organs. This finding is surprising, because it is well known among those who administer cytotoxins such as doxorubicin to patients, that this drug causes severe ulceration of the skin and underlying tissues if allowed to be delivered outside of a vein. After extravasation the drug continues to affect the tissues to such an extent that amputation of limbs in which the extravasation has occurred has been required. So severe is this toxicity that the prescribing information for doxorubicin (and some other similar vesicating drugs) in the Physicians Desk Reference contains a "Box Warning" regarding this danger. The present invention, therefore, provides an effective way to administer chemotherapeutic agents, including highly toxic agents such as doxorubicin, while minimizing the major side effects described above.

BRIEF DESCRIPTION OF THE INVENTION

Broadly, one embodiment of the invention includes a formulation for treating a patient for a neoplasm by inhalation comprising: a safe and effective amount of a vesicant and a pharmaceutically acceptable carrier, preferably the vesicant does not exhibit substantial pulmonary toxicity. In one aspect of the embodiment the vesicant is typically a moderate vesicant such as paclitaxel or carboplatin. A description of such a moderate vesicant would include a non-encapsulated anticancer drug, wherein when 0.2 ml of the drug is injected intradermally to rats, at the clinical concentration for parenteral use in humans: (a) a lesion results that is at least 20 $mm^2$ in area fourteen days after the intradermal injection; and (b) at least 50% of the tested rats have this size of lesion. Other aspects of this broad embodiment typically include a vesicant that is a severe vesicant such as doxorubicin, vincristine, and vinorelbine. The neoplasm to be treated is typically a pulmonary neoplasm, a neoplasm of the head and neck, or other systemic neoplasm. The drug may be in the form of a liquid, a powder, a liquid aerosol, or a powdered aerosol. Typically the patient is a mammal such as a domestic animal or a human. In other aspects the embodiment includes formulations of drugs such as etoposide and a carrier such as DMA. Typically the severe vesicant is an anthracycline such as epirubicin, daunorubicin, methoxymorpholinodoxorubicin, cyanomorpholinyl doxorubicin, doxorubicin, or idarubicin; or a vinca alkaloid such as vincristine, vinorelbine, vinorelbine, vindesine, or vinblastine. In other formulations the drug is typically mechlorethamine, mithramycin, dactinomycin, bisantrene, or amsacrine. Typically the formulation may include a taxane such as paclitaxel, its derivatives and the like. Typical animal and human doses are provided in the tables and text below.

A further broad embodiment of the invention includes a formulation for treating a patient having a neoplasm by inhalation comprising: a safe and effective amount of a non-encapsulated antineoplastic drug having a molecular weight above 350, that does not exhibit substantial pulmonary toxicity; and an effective amount of a pharmaceutically acceptable carrier. The neoplasm treated with the formulation is typically a pulmonary neoplasm, a neoplasm of the head and neck, or a systemic neoplasm. The drug used in the formulation is in the form of a liquid, a powder, a liquid aerosol, or a powdered aerosol. Typically the drug has a protein binding affinity of 25% or 50% or more. Further the drug can typically have a higher molecular weights such as above 400, 450, or 500 daltons. Typical animal and human doses are provided in the tables and text below.

In a yet further embodiment of the invention, there is disclosed a formulation for treating a patient for a neoplasm by inhalation comprising: a safe and effective amount of a taxane in an effective amount of vehicle comprising polyethyleneglycol (PEG) and an alcohol. Typically the formulation will also contain an acid, where the acid present in amount effective to stabilize the taxane. Typically the alcohol is ethanol, and the acid is an inorganic acid such as HCl, or an organic acid such as citric acid and the like. In some typical formulations the taxane is paclitaxel and the formulation contains about 8% to 40% polyethyleneglycol, about 90% to 60% alcohol, and about 0.01% to 2% acid. Typical animal and human doses are provided in the table and text below.

Another embodiment provides for formulations for treating a patient for a neoplasm by inhalation comprising: a safe and effective amount of a drug selected from the group consisting of carmustine, dacarbazine, melphalan, mercaptopurine, mitoxantrone, esorubicin, teniposide, aclacinomycin, plicamycin, streptozocin, and menogaril; and a safe and effective amount of a pharmaceutically effective carrier, wherein the drugs do not exhibit substantial pulmonary toxicity.

A yet further embodiment provides for a formulation for treating a patient for a neoplasm by inhalation comprising: a safe and effective amount of a drug selected from the group consisting of estramustine phosphate, geldanamycin, bryostatin, suramin, carboxyamido-triazoles; onconase, and SU101 and its active metabolite SU20; and a safe and effective amount of a pharmaceutically effective carrier, wherein the drugs do not exhibit substantial pulmonary toxicity.

A still further embodiment provides for a formulation for treating a patient for a neoplasm by inhalation comprising: a safe and effective amount of etoposide and an effective amount of a DMA carrier. Typical animal and human doses are provided in the tables and text below.

Another embodiment includes a formulation for treating a patient for a neoplasm by inhalation comprising: a safe and effective amount of a microsuspension of 9-aminocamptothecin in an aqueous carrier. Typical anima and human doses are provided in the tables and text below.

A further broad embodiment of the invention includes a formulation for treating a patient having a neoplasm comprising: administering to the patient by inhalation, (1) an effective amount of a highly toxic antineoplastic drug; and (2) an effective amount of a chemoprotectant, wherein the chemoprotectant reduces or eliminates toxic effects in the patient that are a result of administering the highly toxic antineoplastic drug. Typically the chemoprotectant reduces or eliminates systemic toxicity in the patient, and/or reduces or eliminates respiratory tract toxicity in the patient. Typically the formulation includes a chemoprotectant such as dexrazoxane (ICRF-187), mesna (ORG-2766), ethiofos (WR2721), or a mixture thereof. The chemoprotectant may be administered before, after, or during the administration of the antineoplastic drug. The antineoplastic drug used with the chemoprotectant may be a nonvesicant, moderate vesicant, or a severe vesicant. Typical among the drugs with which the chemoprotectant is useful are bleomycin, doxorubicin, and mitomycin-C.

The invention also typically includes a method for treating a patient having a neoplasm comprising: administering to the patient by inhalation, (1) an effective amount of a highly toxic antineoplastic drug; and (2) an effective amount of a chemoprotectant, wherein the chemoprotectant reduces or eliminates toxic effects in the patient that are a result of administering the highly toxic antineoplastic drug. Typically the chemoprotectant reduces or eliminates systemic toxicity in the patient and/or reduces or eliminates respiratory tract toxicity in the patient. Chemoprotectants can typically be dexrazoxane (ICRF-187), mesna (ORG-2766), ethiofos (WR2721), or a mixture thereof. The chemoprotectant may be administered before, after, or during the administration of the antineoplastic drug. Typically the antineoplastic drug is a nonvesicant, a moderate vesicant, or a severe vesicant. Typically the antineoplastic drug comprises bleomycin, doxorubicin, or mitomycin-C.

An additional embodiment of the invention includes a method for treating a patient having a neoplasm comprising: administering a safe and effective amount of a non-encapsulated antineoplastic drug to the patient by inhalation, the drug selected from the group consisting of antineoplastic drugs wherein when 0.2 ml of the drug is injected intradermally to rats, at the clinical concentration for IV use in humans: (a) at least one lesion per rat results which is greater than 20 $mm^2$ in area fourteen days after the intradermal injection; and (b) at least 50% of the tested rats have these lesions. In some typical embodiments when the drug is doxorubicin or vinblastine sulfate, the drug is inhaled in the absence of perfluorocarbon. Typical diseases treated include a neoplasm such as a pulmonary neoplasm, a neoplasm of the head and neck, or other systemic neoplasm. The drug may typically be inhaled as inhaled as a liquid aerosol or as a powdered aerosol. Mammal animals and humans are typical patients treated with the method. The drug may typically be selected from the group consisting of doxorubicin, daunorubicin, methoxymorpholino-doxorubicin, epirubicin, cyanomorpholinyl doxorubicin, and idarubicin. When the drug is a vinca alkaloid it is typically selected from the group consisting of vincristine, vinorelbine, vindesine, and vinblastine. Other useful drugs typically include the alkylating agents mechlorethamine, mithramycin and dactinomycin. Still additional useful drugs typically include bisantrene and amsacrine. The drug can typically be a taxane such as doxitaxel or paclitaxel.

Another embodiment of the invention includes a method for treating a patient having a neoplasm comprising: administering an effective amount of a highly toxic non-encapsulated antineoplastic drug to a patient by inhalation, wherein the molecular weight of the drug is above 350, and the drug has no substantial pulmonary toxicity. Typically the neoplasm is a pulmonary neoplasm, a neoplasm of the head and neck, or a systemic neoplasm. The drug may be inhaled as a liquid aerosol or as a powdered aerosol. Typically the drug has a protein binding affinity of 25%, 50% or more. In one aspect the drug is typically selected from the group comprising doxorubicin, epirubicin, daunorubicin, methoxymorpholinodoxorubicin, cyanomorpholinyl doxorubicin, and idarubicin. If the drug is doxorubicin or vinca alkaloid it may be typically be administered without the presence of a perfluorocarbon. Typically the vinca alkaloid is selected from the group consisting of vincristine, vinorelbine, vindesine, and vinblastine. Typical alkylating agent type drugs include mechlorethamine, mithramycin, dactinomycin. Other topoisomerase II inhibitors include bisantrene or amsacrine.

An additional embodiment includes a method for treating a patient for a neoplasm by the steps of administering an effective amount of an antineoplastic drug to the patient by inhalation; and administering a pharmaceutically effective amount of the same and/or different antineoplastic drug to the patient parenterally. The patient may be treated with one or more adjunct therapies including radiotherapy, immunotherapy, gene therapy, chemoprotective drug therapy.

A further embodiment includes a method for treating a patient for a neoplasm including the steps of administering an effective amount of an antineoplastic drug to the patient by inhalation; and administering an effective amount of the same and/or different antineoplastic drug to the patient by isolated organ perfusion. The patient may be treated by one or more adjunct therapies including radiotherapy, immunotherapy, gene therapy, and chemoprotective drug therapy.

An further embodiment includes a method for treating a patient for a pulmonary neoplasm by the steps of (1) selecting one or more antineoplastic drugs efficacious in treating the neoplasm and having a residence time in the pulmonary mucosa sufficient to be efficacious in the treatment of the pulmonary neoplasm; and (2) administering the drug(s) to the patient by inhalation in a non-encapsulated form. Typically when 0.2 ml of at least one of the drugs is injected intradermally to rats, at the clinical concentration for parenteral use in humans: a lesion results which is greater than 20 $mm^2$ in area fourteen days after the intradermal injection; and B. at least 50% of the tested rats have these lesions. Typically the molecular weight of at least one of the selected drugs is above 350.

A still further embodiment includes a method of use including the steps of administering one or more non-encapsulated highly toxic anticancer drugs to a mammal by inhalation, wherein at least one of the drugs comprises a severe vesicant.

Another embodiment is an apparatus for treating a patient for a neoplasm by inhalation that is a combination of a nebulizer and a formulation for treating a neoplasm, the formulation including (1) a non-encapsulated anticancer drug, and (2) a pharmaceutically acceptable carrier; wherein when 0.2 ml of the formulation is injected intradermally to rats, at the clinical concentration for parenteral use in humans: (a) a lesion results which is greater than about 20 $mm^2$ in area fourteen days after the intradermal injection; and (b) at least 50% of the tested rats have these lesions. A further embodiment includes a formulation which when injected results in a lesion which is greater than about 10 $mm^2$ in area 30 days after the intradermal injection; and at least about 50% of the tested rats have these longer lasting lesions. Typically the formulation includes an anthracycline. Anthracyclines may be selected from the group consisting of epirubicin, daunorubicin, methoxymorpholinodoxorubicin, cyanomorpholinyl doxorubicin, doxorubicin, and idarubicin. The formulation also typically and contain a vinca alkaloid. Vinca alkaloids may be selected from the group consisting of vincristine, vinorelbine, vinorelbine, vindesine, and vinblastine. Alternately, the formulation may contain vesicant selected from the group consisting of mechlorethamine, mithramycin, and dactinomycin; or bisantrene or amsacrine. Typically the formulation can also contain a taxane which is typically a paclitaxel or doxytaxel.

Another embodiment of the invention includes an inhalation mask for administering aerosols to an patient comprising: means for enclosing the mouth and nose of the patient, having an open end and a closed end, the open end adapted for placing over the mouth and nose of the patient; upper and lower holes in the closed end adapted for insertion of a nose outlet tube and a mouth inhalation tube; the nose outlet tube attached to the upper hole, adapted to accept exhaled breath from the nose of the patient; a one way valve in the nose tube adapted to allow exhalation but not inhalation; the mouth inhalation tube having an outer and an inner end, partially inserted through the lower hole, the inner end continuing to end at the rear of the patients mouth, the inhalation tube end cut at an angle so that the lower portion extends further into the patients mouth than the upper portion and adapted to fit the curvature of the rear of the patients mouth; and a y-adapter attached to the outer end of the mouth inhalation tube. The mask typically will have a moderate vesicant or a severe vesicant present in the inhalation tube.

DETAILED DESCRIPTION OF THE INVENTION AND BEST MODE

Figure 1:
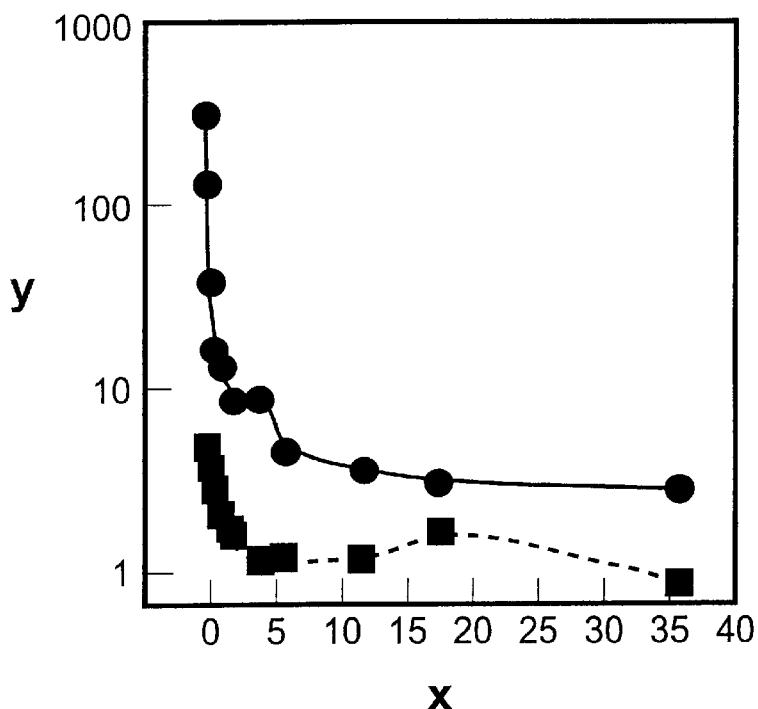
FIG. 1 shows the plasma drug concentration time profile for dog #101 having doxorubicin administered intravenously (IV) (circles) and by the pulmonary inhalation route (IH) (squares). The vertical Y scale is the concentration of drug in the circulatory system in ng/ml and the horizontal X scale is time after treatment in hours.

The delivery of antineoplastic drugs by inhalation by the pulmonary route is an attractive alternative to the administration of drugs by various injectable methods, particularly those drugs that are given on a chronic or repeated administration schedule. A cause of concern is the toxic nature of the drugs particularly those that are cytotoxic such as the classes represented by alkylating agents, taxanes, vinca alkaloids, platinum complexes, anthracyclines and others that are considered particularly toxic especially when administered outside the circulatory system.

Broadly, the inventors have discovered that highly toxic, vesicant and previously unknown nonvesicant antineoplastic drugs can be effectively delivered to a patient in need of treatment for neoplasms or cancers by inhalation. This route is particularly effective for treatment of neoplasms or cancers of the pulmonary system because the highly toxic drugs are delivered directly to the site where they are needed, providing regional doses much higher than can be achieved by conventional IV delivery. As used herein the respiratory tract includes the oral and nasal-pharyngeal, tracheobronchial, and pulmonary regions. The pulmonary region is defined to include the upper and lower bronchi, bronchioles, terminal bronchioles, respiratory bronchioles, and alveoli.

An important benefit from inhalation therapy for neoplasms of the head, neck and respiratory tract, is that exposure to the rest of the body is controlled following administration of high doses of drug and consequently is spared much of the adverse side effects often associated with high doses of systemically administered highly toxic antineoplastic drugs, yet significantly increased doses are provided at the site of the tumor. These toxic effects include for example: cardiotoxicity, myelosuppression, thrombocytopenia, renal toxicity, and hepatic toxicity that are often life threatening. The toxic effects are often so severe that it is not uncommon for patients to die from the effects of the systemically administered drugs rather than from the disease for which they are being treated.

Broadly, vesicants as used herein include chemotherapeutic agents that are toxic and typically cause long lasting damage to surrounding tissue if the drug is extravasated. If inadvertently delivered outside of a vein, a vesicant has the potential to cause pain, cellular damage including cellulitis, tissue destruction (necrosis) with the formation of a long lasting sore or ulcer and sloughing of tissues that may be extensive and require skin grafting. In extreme cases extravasation of vesicants such as doxorubicin has required surgical excision of the affected area or amputation of the affected limb. Examples of antineoplastic chemotherapeutic agents that are generally accepted vesicants include alkylating agents such as mechlorethamine, dactinomycin, mithramycin; topoisomerase II inhibitors such as bisantrene, doxorubicin (adriamycin), daunorubicin, dactinomycin, amsacrine, epirubicin, daunorubicin, and idarubicin; tubulin inhibitors such as vincristine, vinblastine, and vindesine; and estramustine. A partial list of vesicants is found in Table 1.

In another embodiment, vesicants as more narrowly used herein include drugs that produce a lesion in rats, where the average lesion size is greater than about 20 mm² in area, fourteen days after an intradermal injection of 0.2 ml of the drug, and where 50% or more of the animals have this size of lesion. The drug concentration for the intradermal injection is the clinical concentration recommended by the manufacturer for use in humans, the dose recommended in the Physicians Desk Reference, 1997 (or a more current version of this reference), or another drug manual for health specialists. If there is no recommendation by the manufacturer (for example for because the drug is new) and there is no recommendation in the Physicians Desk Reference or similar drug manual for health specialists then other current medical literature may be used. If more than one clinical concentration is recommended, the highest recommended clinical concentration is used. Lesion as used herein means an open sore or ulcer or sloughing off of skin with exposure of underlying tissue.

In a yet further embodiment of the invention, 0.2 ml of a highly toxic anticancer drug (vesicant) at a dose recommended for humans (as discussed above) is administered intradermally to rats at a concentration that causes the above mentioned lesion size for a more extended period of time. That is, the lesions remain above about 10 mm² up to at least 30 days in at least 50% or more of the animals.

Nonvesicants typically are also irritating and can cause pain, but do not usually result in long lasting sores or ulcers or sloughing off of tissues except in exceptional cases.

Examples include alkylating agents such as cyclophosphamide, bleomycin (blenoxane), carmustine, and dacarbazine; DNA crosslinking agents such as thiotepa, cisplatin, melphalan (L-PAM); antimetabolites such as cytarabine, fluorouracil (5-FU), methotrexate (MTX), and mercaptopurine (6 MP); topoisomerase II inhibitors such as mitoxantrone; epipodophyllotoxins such as etoposide (VP-16) and teniposide (VM-26); hormonal agents such as estrogens, glucocorticosteroids, progestins, and antiestrogens; and miscellaneous agents such as asparaginase, and streptozocin.

A listing of materials usually accepted to be vesicants or nonvesicants is provided below as Table 1—Vesicant/Nonvesicant Drug Activity.

TABLE 1

Vesicant/Non-Vesicant Drug Activity

| Classification | Vesicant | Non-Vesicant |
| --- | --- | --- |
| Alkylating Agents | Mechlorethamine[a,c,d,e]* | Cyclophosphamide (Cytoxan)[b] |
| | Mitomycin-C[a,c,e]* | Bleomycin (Blenoxane)[b,e] |
| | Dactinomycin[d,e]* | Carmustine[a,b,d] |
| | Mithramycin[d] (Plicamycin) | Mithramycin[a,b] (Plicamycin) |
| | | Dacarbazine[a,b,e] |
| DNA Crosslinking Agents | | Thiotepa[b] |
| | | Cisplatin[b,e] |
| | | Melphalan (L-PAM)[b] |
| Antimetabolites | | Cytarabine (ARA C)[b] |
| | | Fluorouracil (5 FU)[b,d,e] |
| | | Methotrexate (MTX)[b] |
| | | Mercaptopurine (6 MP)[b] |
| Topoisomerase II Inhibitors | Bisantrene[c,e]* (Anthracene) | Mitoxantrone[b,e] (Anthracene) |
| | Dactinomycin[a,c] | Esorubicin[e] |
| | Doxorubicin[a,b,c,d,e]* (Anthracycline) | Etoposide (VP-16)[a,b,e] (Epipodophyllotoxin) |
| | Cyanomorpholinyl Doxorubicin[e]* | Teniposide (VM-26)[a,b,e] (Epipodophyllotoxin) |
| | Amsacrine[a,c,e]* | |
| | Epirubicin[c,e]* | |
| | Daunorubicin[a,d,e]* | |
| | Idarubicin[a,e]* | |
| | | Liposomal anthracyclines[e] |
| Hormonal Agents | | Estrogens[b] |
| | | Glucocorticosteroids[b] |
| | | Progestins[b] |
| | | Antiestrogens[b] |
| Tubulin Inhibitors | Vinblastine[a,d,e]* | |
| | Vincristine[a,d,e]* | |
| | Vinorelbine[e]* | |
| | Vindesine[a,e]* | |
| | Paclitaxel[c,] | Paclitaxel[e,f] |
| Miscellaneous | | Asparaginase[b] (Enzyme) |
| | | Aclacinomycin[e] |
| | | Streptozocin[a,b] |
| | | Menogaril[e] |

[a]According to U.S. Pat. No. 5,602,112
[b]Dorr, R.T. et al, Lack of Experimental Vesicant Activity for the Anticancer Agents Cisplatin, Melphalan, and Mitoxantrone, Cancer Chemother. Pharmacol., Vol. 16, 1986, pp. 91–94
[c]According to Bicher, A. et al, Infusion Site Soft-Tissue Injury After Paclitaxel Administration, Cancer, Vol. 76, No. 1, July 1, 1995, pp. 116–120
[d]Rudolph, R. et al; Etiology and Treatment of Chemotherapeutic Agent Extravasation Injuries: A Review; Journal of Clinical Oncology, Vol. 5; No. 7; July 1987; pp. 1116–1126
[e]Bertelli, G., Prevention and Management of Extravasation of Cytotoxic Drugs, Drug Safety, 12 (4) 1995; pp. 245–255. The listed drugs have been reported in at least one case, either clinically or experimentally, to cause tissue necrosis after accidental extravasation.
Symbol: * = vesicants, drugs with the highest potential for localized tissue damage after extravasation
[f]Cancer, R.T., Communications, Author Reply, Cancer, pp. 226

Typical embodiments of the invention use highly toxic antineoplastic drugs that have similar or greater vesicating activity than those that have been tested in animals by inhalation to date. One embodiment typically uses severely vesicating toxic antineoplastic drugs having higher vesicating activity than those represented by 5-FU, β-cytosine arabinoside (Ara-C, cytarabine), mitomycin C, and cisplatin. In respect to the latter, it is disclosed that a highly toxic drug represented by the class anthracyclines (of which doxorubicin is among the most toxic), has been administered by inhalation to a patient in need of treatment for neoplasms. In a further embodiment of the invention it is disclosed that vesicants other than doxorubicin can be given to patients by inhalation. In respect to the latter, highly toxic drugs represented by the classes vinca alkaloids, and taxanes, having similar high toxicities have been administered by inhalation to a patient in need of treatment for neoplasms. In a yet further embodiment of the invention there is disclosed that certain antineoplastic drugs that are nonvesicants can be administered by inhalation to a patient in need of treatment for neoplasms. In a further embodiment of the invention there are disclosed formulations and methods for applying the aforementioned highly toxic drugs to a patient in need of treatment for pulmonary neoplasms by inhalation.

EXAMPLE 1

This example illustrates and confirms toxicity and vesicant/nonvesicant activity of several antineoplastic drugs. The vesicant activities of thirteen anticancer drugs were investigated (see the listing in Table 2 below). Doxorubicin has traditionally been considered a vesicant (see Table 1). Paclitaxel has previously been considered a nonvesicant, but recent literature has advocated its classification as a vesicant. Some of the remaining drugs are traditionally considered to be vesicants and others nonvesicants (Table 1). Day fourteen after injection was chosen as the time for comparison for vesicant activity, because lesions caused by nonvesicants should have been significantly reduced while lesions caused by vesicants should still be large. Sterile saline solution (0.9%) for injection USP, pH 4.5–7.0, or sterile water for injection, as appropriate, was used to reconstitute the drugs.

The drugs used for the vesicant activity tests are identified as follows: doxorubicin (Adriamycin PFS), a red liquid in glass vials, no formulation was necessary; cisplatin (Platinol-AQ™), a liquid in glass vials, no formulation was necessary; Paclitaxel (Taxol™), a liquid in glass vials, formulated with saline solution; fluorouracil, a clear yellow liquid in glass vials, no formulation was necessary; cytarabine (Cytosar-U™), a white powder in glass vials, formulated with water; 9-aminocamptothecin (9-AC colloidal suspension), a yellow powder in glass vials, formulated with water; cyclophosphamide (Cytoxan™), a yellow powder in glass vials, formulated with a saline/water mixture; carboplatin (Paraplatin™), a white powder in injectable vials, formulated with saline solution; etoposide (VePesid™), a clear liquid in glass vials, formulated with saline solution; bleomycin (bleomycin sulfate, USP), a lyophilized powder tablet in glass vials, formulated with saline solution; vincristine (vincristine sulfate), an injectable liquid in injection vials, no formulation necessary; vinorelbine tartrate (Navelbine™), a clear liquid in glass vials, diluted with water per package instructions; and mitomycin (Mutamycin™), a gray crystalline powder in glass amber bottles, formulated with water. All of these drugs were reconstituted following standard and known methods recommended by the manufacturers.

The tests for vesicant activity were conducted using Sprague Dawley rats (7–8 weeks old having 150–200 g of body weight. Each received a single intradermal injection of the test drug at the recommended clinical concentration (listed below in Table 2) in the right dorsum. Approximately 24 hours prior to administration, the hair was removed from the dorsum using clippers and a depilatory agent. Each 0.2 ml injection was given with a 1 ml syringe and 27 gauge needle. All drug solutions were either isotonic or slightly hypertonic.

TABLE 2

Formulations administered for Vesicant Tests

| Test Formulation | Formulation Concentration |
|---|---|
| 1 Doxorubicin | 2 mg/ml |
| 2 Platinol | 1 mg/ml |
| 3 Paclitaxel | 1.2 mg/ml |
| 4 Fluorouracil | 50 mg/ml |
| 5 Cytarabine | 100 mg/ml |
| 6 9-aminocamptothecin | 100 μg/ml |
| 7 Cyclophosphamide | 20 mg/ml |
| 8 Carboplatin | 10 mg/ml |
| 9 Etoposide | 0.4 mg/ml |
| 10 Bleomycin | 20 units/ml |
| 11 Vincristine | 1 mg/ml |
| 12 Vinorelbine | 3 mg/ml |
| 13 Mitomycin-C | 0.5 mg/ml |

Table 3 below is a tabulation of the resultant lesion sizes that developed from intradermal injections of the above drugs. Lesion sizes were measured as more fully discussed below.

TABLE 3

Individual Lesion Size Measurements ($mm^2$)
(see text for explanation of measurements)

| Animal Number | Test Drug | Day of Test (post injection) 6 | 8 | 10 | 13 | 15 | 17 | 20 | 22 | 24 | 27 | 29 | 31 | 34 | 36 | 38 | 41 |
|---|---|---|---|---|---|---|---|---|---|---|---|---|---|---|---|---|---|
| 101 | Doxorubicin | — | 21.4 | 33.9 | 57.0 | 42.9 | 34.0 | 35.4 | 27.2 | 32.2 | 31.7 | 31.7 | 17.1 | 8.3 | 6.3 | 6.7 | 4.5 |
| 102 | Doxorubicin | — | 18.8 | 23.5 | 10.9 | 12.9 | 9.7 | 10.2 | 9.9 | 11.8 | 10.5 | 9.9 | 10.2 | 2.8 | — | — | — |
| 103 | Doxorubicin | — | 36.5 | 58.0 | 82.9 | 45.5 | 37.7 | 28.1 | 26.9 | 21.0 | 23.9 | 18.6 | 16.2 | 12.5 | 10.3 | 7.6 | 6.1 |
| 104 | Doxorubicin | — | 44.6 | 27.3 | 33.6 | 17.7 | 21.7 | 28.1 | 19.5 | 16.6 | 16.1 | 18.9 | 13.9 | 9.0 | 5.1 | 4.5 | 4.0 |
| 105 | Doxorubicin | — | 33.9 | 35.2 | 33.3 | 35.1 | 29.4 | 30.2 | 29.7 | 25.0 | 24.4 | 24.8 | 23.5 | 24.0 | 24.5 | 21.6 | 22.0 |
| 106 | Doxorubicin | — | 30.6 | 43.2 | 32.2 | 35.2 | 34.4 | 29.2 | 30.2 | 15.5 | 16.0 | 15.4 | 14.5 | 16.2 | 14.8 | 14.3 | 5.2 |
| 107 | Doxorubicin | — | 26.1 | 39.7 | 38.6 | 33.8 | 31.3 | 25.0 | 22.0 | 21.6 | 19.8 | 22.4 | 21.5 | 20.9 | 21.0 | 18.4 | 18.9 |
| 111 | Platinol | 26.9 | 18.7 | 18.0 | 11.8 | 21.2 | 17.1 | 6.9 | 1.5 | 1.0 | — | — | — | — | — | — | — |

TABLE 3-continued Individual Lesion Size Measurements (mm$^2$)
(see text for explanation of measurements)

| Animal Number | Test Drug | \multicolumn{16}{c}{Day of Test (post injection)} |
| --- | --- | --- | --- | --- | --- | --- | --- | --- | --- | --- | --- | --- | --- | --- | --- | --- | --- |
| | | 6 | 8 | 10 | 13 | 15 | 17 | 20 | 22 | 24 | 27 | 29 | 31 | 34 | 36 | 38 | 41 |
| 112 | Platinol | 35.5 | 20.3 | 20.8 | 15.5 | 16.1 | 16.2 | 16.5 | 4.1 | — | — | — | — | — | — | — | — |
| 113 | Platinol | 15.3 | 15.8 | 14.6 | 10.1 | 9.1 | 9.0 | 8.3 | 2.9 | 2.6 | 1.7 | — | — | — | — | — | — |
| 114 | Platinol | 17.2 | 11.3 | 13.2 | 9.7 | 9.2 | 10.3 | 10.5 | 9.1 | — | — | — | — | — | — | — | — |
| 115 | Platinol | 26.8 | 25.0 | 14.8 | 21.8 | 18.0 | 15.0 | 16.0 | 16.0 | 2.1 | 1.7 | 1.4 | — | — | — | — | — |
| 116 | Platinol | 21.8 | 20.7 | 12.2 | 11.8 | 12.9 | 12.6 | 8.4 | 10.8 | 8.5 | 8.4 | — | — | — | — | — | — |
| 117 | Platinol | 24.9 | 21.3 | 16.7 | 15.1 | 16.4 | 14.8 | 14.3 | 12.2 | 12.5 | 2.8 | — | — | — | — | — | — |
| 121 | Taxol | 23.7 | 21.6 | 21.2 | 18.9 | 3.5 | — | — | — | — | — | — | — | — | — | — | — |
| 122 | Taxol | 37.3 | 30.1 | 26.1 | 25.2 | 21.8 | 21.7 | 5.6 | 2.1 | 1.8 | — | — | — | — | — | — | — |
| 123 | Taxol | 7.9 | 5.9 | 4.3 | 1.1 | 1.2 | — | — | — | — | — | — | — | — | — | — | — |
| 124 | Taxol | 43.2 | 36.9 | 32.9 | 30.6 | 29.0 | 28.5 | — | — | — | — | — | — | — | — | — | — |
| 125 | Taxol | 38.4 | 34.6 | 28.6 | 22.1 | 5.9 | — | — | — | — | — | — | — | — | — | — | — |
| 126 | Taxol | 69.5 | 59.5 | 53.3 | 53.3 | 42.9 | 5.2 | — | — | — | — | — | — | — | — | — | — |
| 127 | Taxol | 45.9 | 23.1 | 16.1 | 14.3 | 8.4 | 5.0 | — | — | — | — | — | — | — | — | — | — |
| 131 | Fluorouracil | 29.0 | 19.9 | 13.5 | 11.2 | 14.3 | 11.6 | 8.3 | 2.0 | — | — | — | — | — | — | — | — |
| 132 | Fluorouracil | 17.1 | 16.2 | 11.8 | 3.0 | — | — | — | — | — | — | — | — | — | — | — | — |
| 133 | Fluorouracil | 27.0 | 23.8 | 17.4 | 17.6 | 17.9 | 0.5 | — | — | — | — | — | — | — | — | — | — |
| 134 | Fluorouracil | 21.9 | 18.9 | 17.0 | 6.7 | — | — | — | — | — | — | — | — | — | — | — | — |
| 135 | Fluorouracil | 20.5 | 27.5 | 21.4 | 4.5 | — | — | — | — | — | — | — | — | — | — | — | — |
| 136 | Fluorouracil | 23.5 | 14.0 | 10.1 | 9.5 | 8.0 | 7.8 | 1.8 | — | — | — | — | — | — | — | — | — |
| 137 | Fluorouracil | 20.5 | 7.0 | 6.2 | 4.8 | 4.6 | 3.8 | — | — | — | — | — | — | — | — | — | — |
| 151 | 9-aminocamptothecin | 21.8 | 15.8 | 16.0 | 14.5 | 9.0 | 19.9 | — | — | — | — | — | — | — | — | — | — |
| 152 | 9-aminocamptothecin | 8.6 | 4.4 | 5.4 | 3.7 | 4.0 | 3.6 | — | — | — | — | — | — | — | — | — | — |
| 153 | 9-aminocamptothecin | 4.4 | 2.6 | 2.9 | 1.3 | 1.1 | — | — | — | — | — | — | — | — | — | — | — |
| 154 | 9-aminocamptothecin | 23.8 | 21.9 | 20.9 | 19.8 | 15.5 | 18.6 | — | — | — | — | — | — | — | — | — | — |
| 155 | 9-aminocamptothecin | 12.5 | 7.9 | 10.0 | 9.6 | 9.9 | 0.6 | — | — | — | — | — | — | — | — | — | — |
| 156 | 9-aminocamptothecin | 12.6 | 10.4 | 5.8 | 4.6 | 3.1 | — | — | — | — | — | — | — | — | — | — | — |
| 157 | 9-aminocamptothecin | 12.5 | 7.8 | 5.2 | 3.7 | — | — | — | — | — | — | — | — | — | — | — | — |
| 161 | Cyclophosphamide | 16.4 | 13.6 | 11.3 | 9.4 | 8.3 | 8.6 | — | — | — | — | — | — | — | — | — | — |
| 162 | Cyclophosphamide | 35.1 | 33.8 | 23.2 | 3.5 | 1.4 | — | — | — | — | — | — | — | — | — | — | — |
| 163 | Cyclophosphamide | 25.8 | 18.9 | 21.0 | 19.3 | 17.2 | 17.2 | 12.1 | 12.5 | 14.0 | 7.8 | 2.4 | — | — | — | — | — |
| 165 | Cyclophosphamide | 19.4 | 18.2 | 17.9 | 17.4 | 16.6 | 15.9 | 13.2 | 12.2 | 12.7 | 7.5 | 1.8 | 1.5 | — | — | — | — |
| 166 | Cyclophosphamide | 31.8 | 33.8 | 25.4 | 23.9 | 11.9 | 2.2 | — | — | — | — | — | — | — | — | — | — |
| 167 | Cyclophosphamide | 25.2 | 19.7 | 19.1 | 19.3 | 18.9 | 18.9 | 17.4 | 14.6 | 15.6 | 4.1 | 2.0 | — | — | — | — | — |
| 171 | Carboplatin | 16.2 | 17.3 | 12.2 | 10.9 | 10.4 | 8.1 | 4.6 | 0.8 | — | — | — | — | — | — | — | — |
| 172 | Carboplatin | 9.0 | 5.1 | 21.9 | 17.5 | 7.6 | 4.1 | 5.2 | 6.2 | 5.9 | 5.2 | 3.2 | 2.6 | — | — | — | — |
| 173 | Carboplatin | 24.8 | 23.4 | 17.7 | 20.5 | 18.5 | 16.0 | 8.6 | 3.4 | 0.8 | 0.6 | — | — | — | — | — | — |
| 174 | Carboplatin | 31.9 | 23.1 | 18.2 | 24.2 | 27.0 | 19.4 | 15.5 | 13.1 | 11.2 | 4.0 | 1.5 | — | — | — | — | — |
| 175 | Carboplatin | 20.5 | 24.5 | 22.1 | 13.4 | 20.4 | 16.8 | 5.4 | 4.9 | 1.8 | 1.2 | — | — | — | — | — | — |
| 177 | Carboplatin | 42.9 | 39.1 | 30.1 | 31.7 | 32.7 | 32.6 | 35.4 | 34.7 | 34.6 | 23.9 | 25.2 | 25.7 | 19.2 | 0.6 | — | — |
| 181 | Etoposide | 21.1 | 15.0 | 11.2 | 9.2 | 9.8 | 9.0 | 2.9 | — | — | — | — | — | — | — | — | — |
| 182 | Etoposide | — | — | 3.8 | 2.4 | 2.0 | 1.7 | 1.1 | — | — | — | — | — | — | — | — | — |
| 183 | Etoposide | 1.3 | 4.6 | 3.1 | 2.9 | 3.8 | 1.2 | — | — | — | — | — | — | — | — | — | — |
| 184 | Etoposide | — | 9.6 | 4.7 | — | — | — | — | — | — | — | — | — | — | — | — | — |
| 185 | Etoposide | 5.9 | 6.0 | 6.0 | 2.6 | 2.1 | 2.0 | — | — | — | — | — | — | — | — | — | — |
| 186 | Etoposide | 10.6 | 14.1 | 7.7 | 6.6 | 8.4 | 3.8 | 1.7 | — | — | — | — | — | — | — | — | — |
| 187 | Etoposide | 6.5 | 10.0 | 9.3 | 5.3 | 5.4 | 5.1 | 3.5 | — | — | — | — | — | — | — | — | — |
| 191 | Bleomycin | 8.2 | 5.1 | 8.8 | 2.2 | 1.6 | — | — | — | — | — | — | — | — | — | — | — |
| 192 | Bleomycin | 21.1 | 15.3 | 10.8 | 16.3 | 3.8 | 1.3 | — | — | — | — | — | — | — | — | — | — |
| 193 | Bleomycin | 23.5 | 18.9 | 15.4 | 13.8 | 5.5 | 1.3 | — | — | — | — | — | — | — | — | — | — |
| 194 | Bleomycin | — | 5.0 | 3.2 | 1.0 | 2.3 | — | — | — | — | — | — | — | — | — | — | — |
| 195 | Bleomycin | 7.7 | 6.5 | 6.7 | 6.5 | 7.0 | 3.2 | 1.3 | — | — | — | — | — | — | — | — | — |
| 196 | Bleomycin | 13.4 | 7.8 | 6.8 | 7.2 | 6.6 | 0.7 | — | — | — | — | — | — | — | — | — | — |
| 197 | Bleomycin | 27.0 | 27.0 | 26.0 | 25.2 | 26.0 | 24.0 | 1.0 | 0.6 | — | 0.4 | — | — | — | — | — | — |
| 202 | Vincristine | — | — | 469.0 | 307.7 | 227.7 | 160.5 | 109.2 | 93.3 | 93.6 | 83.6 | 67.2 | 57.9 | 47.5 | 40.3 | 40.2 | 34.0 |
| 203 | Vincristine | — | — | — | 165.3 | 158.5 | 67.0 | 29.7 | 28.6 | 24.7 | 21.1 | 22.0 | 22.8 | 27.5 | 30.6 | 21.2 | 13.8 |
| 205 | Vincristine | — | — | — | 130.4 | 136.2 | 111.6 | 76.1 | 61.5 | 58.0 | 42.0 | 26.5 | 18.1 | 12.6 | 5.3 | 4.2 | 1.3 |
| 206 | Vincristine | — | — | 145.6 | 96.9 | 81.6 | 96.1 | 66.7 | 59.2 | 51.3 | 13.0 | 7.2 | — | — | — | — | — |
| 211 | Vinorelbine | — | 16.8 | 421.7 | 315.2 | 289.7 | 274.6 | 250.8 | 200.8 | 170.8 | 159.1 | 237.2 | 243.6 | 243.1 | 219.4 | 180.6 | 149.0 |
| 212 | Vinorelbine | — | 436.7 | 422.1 | 426.5 | 408.5 | 347.6 | 316.8 | 298.8 | 292.4 | 282.0 | 251.0 | 81.3 | 82.0 | 83.9 | 45.8 | 17.2 |
| 213 | Vinorelbine | — | 402.2 | 429.0 | 352.6 | 323.4 | 372.9 | 366.3 | 311.6 | 312.1 | 299.2 | 302.3 | 294.0 | 102.7 | 137.7 | 212.1 | 192.1 |
| 214 | Vinorelbine | — | 322.1 | 261.6 | 283.6 | 293.9 | 241.7 | 227.0 | 221.9 | 227.2 | 105.0 | 86.1 | 72.5 | 65.3 | 71.4 | 52.5 | 62.0 |
| 215 | Vinorelbine | — | 297.0 | 277.8 | 269.7 | 225.3 | 204.2 | 82.5 | 69.8 | 67.8 | 40.0 | 28.4 | 31.9 | 17.4 | 19.2 | 14.0 | 14.5 |
| 216 | Vinorelbine | — | 348.3 | 325.1 | 308.1 | 288.9 | 297.0 | 278.7 | 255.6 | 269.3 | 255.8 | 134.9 | 103.7 | 61.2 | 95.7 | 123.2 | 108.2 |
| 217 | Vinorelbine | — | 275.1 | 309.6 | 272.1 | 249.0 | 217.1 | 208.1 | 209.3 | 190.7 | 175.5 | 173.2 | 172.0 | 173.4 | 157.3 | 187.7 | 155.5 |
| 221 | Mutamycin | 45.0 | 46.8 | 47.5 | 77.0 | 48.2 | 38.8 | 45.4 | 41.6 | 40.3 | 28.6 | 9.6 | 6.4 | 4.1 | 0.7 | — | — |
| 222 | Mutamycin | 50.4 | 50.4 | 49.6 | 41.9 | 45.1 | 34.8 | 42.0 | 46.2 | 9.9 | 9.3 | 7.5 | — | — | — | — | — |
| 223 | Mutamycin | 98.3 | 73.0 | 79.1 | 79.8 | 71.0 | 64.6 | 66.0 | 28.5 | 17.6 | 24.3 | 28.2 | 1.1 | — | — | — | — |
| 224 | Mutamycin | 58.2 | 82.4 | 62.6 | 78.8 | 73.3 | 66.1 | 53.9 | 36.9 | 32.9 | 31.2 | 19.8 | 16.8 | 15.5 | 16.8 | 21.0 | 25.6 |
| 225 | Mutamycin | 28.1 | 24.2 | 28.0 | 19.8 | 29.8 | 23.0 | 12.8 | 13.2 | 11.9 | 8.5 | 6.6 | 7.2 | 2.0 | 1.5 | — | — |
| 226 | Mutamycin | 61.3 | 53.3 | 59.9 | 49.7 | 48.9 | 38.0 | 39.5 | 42.1 | 40.6 | 23.0 | 5.6 | 4.8 | 4.6 | 4.6 | 1.2 | — |
| 227 | Mutamycin | 36.0 | 35.8 | 37.8 | 37.8 | 39.7 | 33.8 | 31.1 | 13.9 | 10.9 | 7.9 | 8.1 | 2.9 | — | — | — | — |

Results were as follows:
1. Abrasions of the dorsal body were observed in a majority of animals for all drugs except cytarabine.
2. Alopecia of the dorsal body was seen for doxorubicin (3/7), paclitaxel (7/7), and fluorouracil (7/7), etoposide (7/7), bleomycin (7/7), vincristine (2/7), vinorelbine (7/7), and mitomycin-C (mutamycin) (4/7).
3. Discoloration of the skin around the site of injection was seen for doxorubicin, vincristine, vinorelbine, and mitomycin-C.
4. Rough coat was observed in fluorouracil (1/7), vincristine (4/7), and vinorelbine (2/7).
5. Systemic effects were observed only for vincristine. Three animals had to be removed from the tests because of their poor condition.
6. Slight edema was observed for all groups. Moderate edema was observed in doxorubicin, vincristine, vinorelbine, and mitomycin-C treated animals. Severe edema was observed only for animals treated with vinorelbine and vincristine.
7. Severe erythema was seen for all drugs except for cisplatin (platinol) and cytarabine.
8. Dermal lesions were observed for all drugs except for cytarabine. Most lesions appeared between days 6 and 10 and maximized in size during the first seven days, and then gradually decreased in size. Doxorubicin, vincristine, vinorelbine, and mitomycin-C were the only drugs that caused lesions that lasted until the test termination at day 41. However, for mitomycin-C only one animal of seven still had lesions to the end of the test. One rat (#123) injected with paclitaxel (taxol) was determined to not have received a proper intradermal injection and was not used in the results.

Dermal lesions at the site of injection were determined to be the best and most objective measure and predictor of vesicant activity for a drug. Lesion size was quantitated by micrometer measurements of the two largest perpendicular diameters and the two values multiplied to yield a lesion area in $mm^2$. Lesions were regularly evaluated and scored as shown in Table 3.

A vesicant as determined by the methods used herein is defined as causing a lesion of at least about 20 $mm^2$, in at least one half of the animals, two weeks after injection (day 15 in Table 3). Table 3 shows that doxorubicin, paclitaxel, carboplatin, vincristine, vinorelbine, and mitomycin-C fulfill these criteria. Cisplatin, etoposide, bleomycin, cytarabine, cyclophosphamide, fluorouracil, and 9-aminocamptothecin are thus categorized as non-vesicants.

A moderate vesicant as determined by the methods used herein is defined as causing a lesion of at least about 20 $mm^2$, in at least one half of the animals, two weeks after injection (day 15 in Table 3), but less than half of the animals will have lesions greater than about 10 $mm^2$ 30 days after injection (day 31 in Table 3). The data from Table 3 shows that paclitaxel, carboplatin, and mitomycin-C fulfill these criteria. Of these, mitomycin-C has been determined to exhibit substantial pulmonary toxicity.

A severe vesicant as determined by the methods used herein is defined as causing a lesion of at least about 20 $mm^2$, in at least one-half of the animals, two weeks after injection (day 15 in Table 3), and at least one-half of the animals will still have lesions greater than about 10 $mm^2$, 30 days after injection (day 31 in Table 3). Table 3 shows that doxorubicin, vincristine, and vinorelbine satisfy these criteria.

Surprisingly it has now been found that moderate to severe vesicants can be used for inhalation therapy of cancer as revealed in the discussion and examples below. Further, other highly toxic drugs, although not having the severity of reaction of moderate to severe vesicants have also been found to be useful in the treatment of cancer by inhalation as further discussed below.

Antineoplastic drugs that are highly toxic and useful in an embodiment of the present invention include the anthracyclines (e.g. doxorubicin, epirubicin, idarubicin, methoxy-morpholinodoxorubicin, daunorubicin, and the like); vinca alkaloids (e.g. vincristine, vinblastine, vindesine, and the like); alkylating agents (e.g. mechlorethamine and the like); carboplatin; nitrogen mustards (e.g. melphalan and the like), topoisomerase I inhibitors (e.g. 9-aminocamptothecin, camptothecin, topotecan, irenotecan, 9-NO-camptothecin, and the like); topoisomerase II inhibitors (e.g. etoposide, teniposide, and the like); and paclitaxel and the like. These and other useful compounds are further discussed below.

In yet a further embodiment of the invention, there are disclosed formulations and methods for applying an appropriate selection of highly toxic drugs that are efficacious in treating the neoplasm or cancer, that are applied by inhalation and that reside in the pulmonary system for a time sufficient to increase the exposure of the neoplasm to the drug, yet allow a reduction and/or controlled systemic exposure of the drug, and provide a more efficacious treatment for pulmonary neoplasms.

In a further embodiment of the invention, it is disclosed that it is possible to deliver antineoplastic drugs by the pulmonary route as a means to provide systemic treatment of distant tumors. The inventors have shown that for selected drugs inhalation can be used as a noninvasive route of delivery without causing significant toxicity to the respiratory tract. This is in contrast with the prior art that used inhalation for treatment of disease in the respiratory system.

As used herein the term patient includes a mammal including, but not limited to, mice, rats, cats, horses, dogs, cattle, sheep, apes, monkeys, goats, camels, other domesticated animals, and of course humans.

Administration by inhalation as used herein includes the respiratory administration of drugs as either liquid aerosols or powdered aerosols suspended in a gas such as air or other nonreactive carrier gas that is inhaled by a patient. Non-encapsulated drug as used herein means that the antineoplastic drug is not enclosed within a liposome, or within a polymeric matrix, or within an enclosing shell. Where the term encapsulated drug is used herein the term means that the antineoplastic drug is enclosed within a liposome, within a polymeric matrix, or within an enclosing shell. However, in some embodiments the antineoplastic drug may be coupled to various molecules yet is still not enclosed in a liposome, matrix or shell as further discussed below.

In other embodiments of the invention the antineoplastic drugs disclosed herein may be coupled with other molecules through ester bonds. Enzymes present in the respiratory system later cleave the ester bonds. One purpose of coupling the antineoplastic drugs through an ester bond is to increase the residence time of the antineoplastic drug in the pulmonary system. Increased residence time is achieved by: first, an increase in molecular weight due to the attached molecule; second, by appropriate choice of a coupled molecule; third, other factors such as for example charge, solubility, shape, particle size of the delivered aerosol, and protein binding can be modified and used to alter the diffusion of the drug. Molecules useful for esterification with the drug include alpha-hydroxy acids and oligomers thereof, vitamins such as vitamins A, C, E and retinoic acid, other retinoids, ceramides, saturated or unsaturated fatty acids such as linoleic acid and glycerin. Preferred molecules for esterification are those naturally present in the area of deposition of the active drug in the respiratory tract.

As a demonstration of the proof of concept, doxorubicin was used in a series of tests. Doxorubicin was chosen as an initial test agent since it is one of most cytotoxic and potent vesicants of all anti-neoplastic agents considered in the broad embodiment (pulmonary delivery of anti-neoplastic drugs) of the present invention. Based on positive outcome of these proof of concept studies, anticancer drugs from other major classes were simultaneously tested. Results consistently showed that using the approach and methods described in this invention the drug could be safely and effectively delivered by inhalation. In Examples 2 and 3 below, doxorubicin was administered to three dogs (beagles) by both the pulmonary and intravenous route of administration. The dogs were given a clinically effective dosage of the drug and the amount of the drug appearing in the blood system was measured.

An anthracycline antineoplastic drug, a salt of doxorubicin, doxorubicin HCl, available from Farmitalia Carlo Erba (now Pharmacia & Upjohn), Milan, Italy, was used in some of the examples herein. The liquid formulation that was administered to the dogs by inhalation of an aerosol was obtained by mixing the doxorubicin hydrochloride with a mixture of ethanol/water at a doxorubicin concentration of approximately 15–25 mg/ml. Typically solutions of 5–75% ethanol are preferred. Water/ethanol ratios may be adjusted to select the desired concentration of doxorubicin and the desired particle size of the aerosol.

EXAMPLE 2

Three adult, male, beagle dogs were used in the tests. The dogs (designated dog 101, 102, and 103) had body weights of 10.66, 10.24, and 10.02 kg respectively. As used herein "$m^2$" used alone with reference to dose refers to square meters in terms of the body surface area of a treated animal or patient, at other times it is qualified in terms of lung surface area. The dogs were given a slow IV infusion treatment of the anthracycline drug doxorubicin HCl at the recommended initial clinical dose (for dogs) of 20 mg/$m^2$ or 1 mg/kg of body weight. A 1 mg/ml drug solution was administered at a rate of 2.0 ml/kg/hr for 30 minutes. The 30-minute infusion interval simulated the time/dose exposure relationship of the inhalation group in Example 3 below. A series of blood samples were taken to characterize the IV pharmacokinetics at predose, 2, 5, 10, 30, 60, 90 minutes and 2, 4, 6, 12, 18, and 36 hours post dosing. Additional blood samples were collected for clinical pathology evaluations on days 3 and 7 of the IV treatment. Changes in blood chemistry and hematology were as expected with administration of doxorubicin HCl at these doses.

EXAMPLE 3

The three dogs used in Example 2 were allowed a one-week washout period before being subjected to exposure to the anthracycline drug doxorubicin HCl by inhalation. The dogs were acclimated to wearing masks for administration of the aerosol prior to treatment. The dogs were exposed to an aerosol concentration of drug sufficient to deposit a total dose of about 10 mg (1 mg/kg). Based on aerosol dosimetry models, approximately one half of this dose was deposited within the respiratory tract. The total dose was about equal to the dosage administered by IV infusion. The dose was calculated using the following equation:

Dose={Drug Conc. (mg/liter)×Mean minute Vol. (liter/min)×Exposure Duration (min)×Total Deposition Fraction (%)}÷Body Weight (kg)

wherein

Mean Min. Vol.=Tidal volume×minute respiratory rate

Exposure Duration=30 min

Mean Body Weight=weight in kg for each dog

Total Deposition Fraction=60% (determined by particle size and respiratory tract deposition models from the published literature such as "Respiratory Tract Deposition of Inhaled Polydisperse Aerosols in Beagle Dogs", R. G. Cuddihy et al, Aerosol Science, Vol 4, pp. 35–45 (1973) and "Deposition and Retention Models for Internal Dosimetry of the Human Respiratory Tract", Task Group on Lung Dynamics, Health Physics, Vol. 12, pp. 173–207 (1966).

Pulmonary function measurements (respiratory rate, tidal volume, and minute volume (calculated)) were monitored during a 30 minute inhalation exposure session. These data provided an estimate of each animal's inspired volume during exposure, and were used to calculate the mass of drug deposited in the respiratory tract.

A series of blood samples were collected at the end of the exposure to characterize the pharmacokinetics. Clinical pathology evaluations were conducted on the third day. All three dogs were necropsied on the third day.

Figure 4:
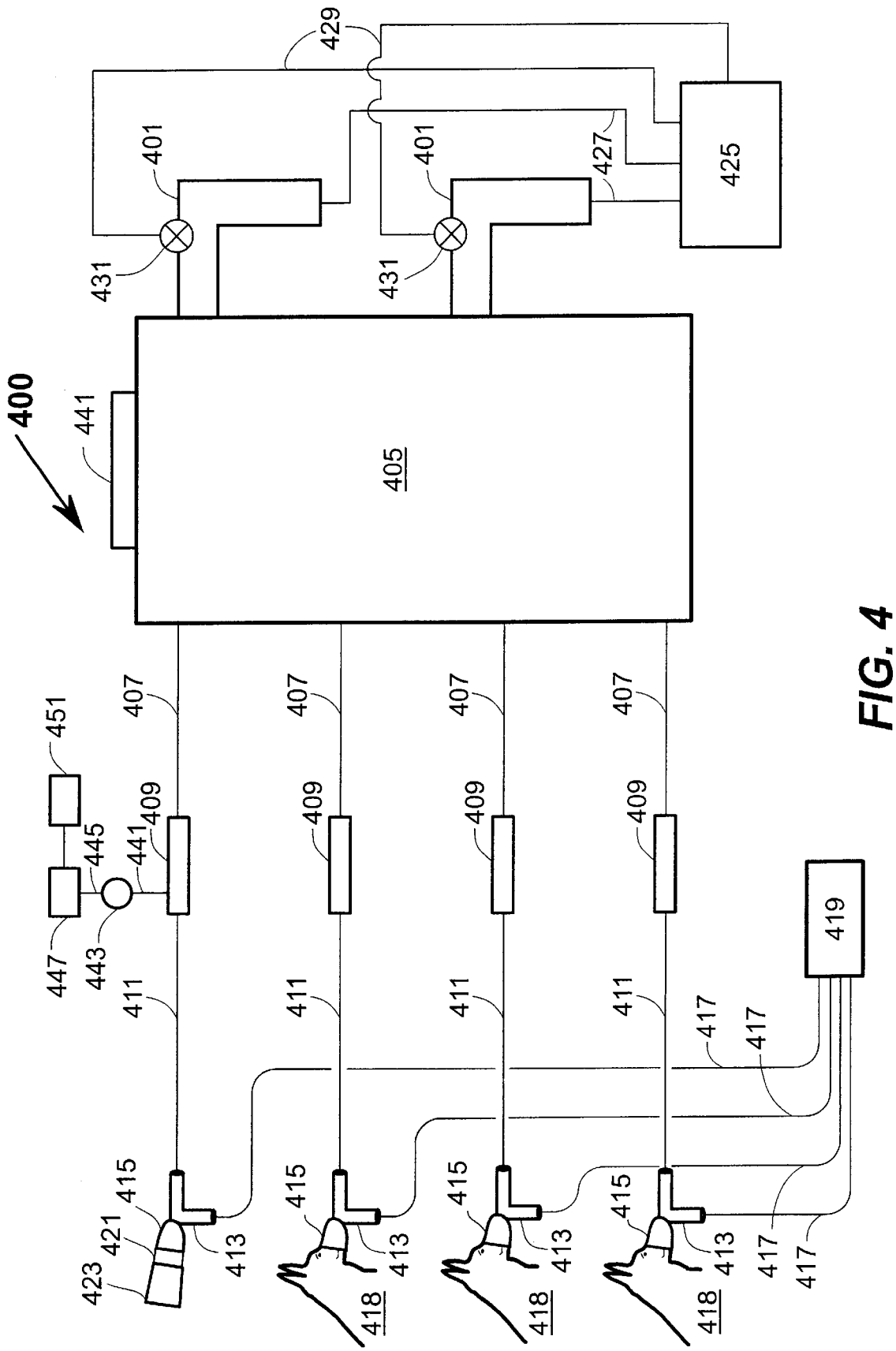
FIG. 4 shows a schematic of the pulmonary delivery apparatus arrangement that was used to administer drug to dogs by inhalation for Example 3.

Referring now to FIG. 4, the drug formulation was administered to the dogs of Example 3 with drug exposure system 400. The drug was aerosolized with two Pari LC Jet Plus™ nebulizers 401. The nebulizer was filled with a solution of 15 mg doxorubicin per ml of 50% water/50% ethanol. The output of each nebulizer 401 was continuous and set to provide the required concentration of aerosol in attached plenum 405. The nebulizers 401 were attached directly to plenum 405 that had a volume of approximately 90 liters. Plenum 405 was connected by four tubes 407 to four venturi 409, respectively, and subsequently connected to four Y-fittings 413 by additional tubing 411. Typical venturi were used to measure the inhaled volume of drug formulation. One end of each of the Y-fittings 411 interfaced with a dog breathing mask 415 while the other end of Y-fitting 411 was connected to tubing 417 leading to an exhaust pump 419. During the tests three dogs 418 were fitted with three of the breathing masks 415. A collection filter 421 was placed in the remaining mask 415. A vacuum pump 423 that drew 1 liter per minute of air for 3 minutes was used in the place of a dog to draw aerosol in order to monitor and measure the amount of drug administered. The vacuum pump was activated four times during the 30-minute administration of drug to the dogs and the amount of drug trapped by the filter set forth in Table 5 below.

A flow of air was supplied to each of the nebulizers 401 from a supply of air 425 via lines 427. Additional air for providing a bias flow of air through the system and for the breathing requirements of the dogs was provided from air supply 425 by supply lines 429 connected to one way valves 431. The one way valves 431 were connected to the upper portion of the nebulizers 401. This additional supply of air provided a continuous flow of air through the system 400 from the air supply 425 to the exhaust pump 417. Alternatively one could eliminate the extra supply of air from supply lines 429 to one way valves 431 and let ambient room air enter the one way valves from the suction action of the nebulizers 401. A Hepa filter 441 mounted to the top of plenum 405 allowed room air to flow in and out of plenum 405 and assured that there was always ambient pressure in the plenum. There was a continuous flow of air containing the aerosol past the masks of the dogs and the dogs were able to breathe air containing the aerosol on demand. An inner tube 621 located within dog breathing mask 415 extended into the mouth of the dogs and was provided with an extension 633 at its lower portion that served to depress the tongue of the dogs to provide an open airway for breathing. See the discussion of FIG. 6 below.

40% as before to obtain the total dose deposited, and reduced by 50% again to obtain the total deposited pulmonary dose. The pulmonary doses obtained by this method of 0.47, 0.56, and 0.53 mg/kg for dogs 101, 102, and 103 respectively compare well with the earlier calculated figures in Table 4.

TABLE 4

TOTAL MASS DATA

| Dog No. | Dog Weight (kg) | Total Inhaled Vol. (l) For 30 Min. | Inhaled Air Aerosol Conc. (mg/l) | Deposition Fraction | Test Art. Fraction | Inhaled Dose (mg/kg) | Deposited Dose (mg/kg) | Pulmonary Dose (mg/kg) |
|---|---|---|---|---|---|---|---|---|
| 101 | 10.66 | 77.5 | 0.250 | 0.60 | 0.937 | 1.70 | 1.02 | 0.51 |
| 102 | 10.24 | 86.8 | 0.250 | 0.60 | 0.937 | 1.99 | 1.19 | 0.60 |
| 103 | 10.02 | 80.8 | 0.250 | 0.60 | 0.937 | 1.89 | 1.13 | 0.57 |
| | A | B | C | D | E | | | |

Each of the four venturi 409 were connected by line 441 to a pressure transducer 443 (the one shown is typical for the four venturi) that was used to measure pressure differences across the venturi. The pressure transducers 443 were connected by line 445 to an analog amplifier 447 to increase the output signal and prepare the signal sent via line 449 to computer system 451. Computer system 451 is a desk model PC of typical design in the industry and can be used in conjunction with a BUXCO or PO-NE-MAH software program to calculate the uptake of air containing aerosol and thus the drug dosage by each of the dogs.

Table 4 below summarizes the exposure data for doxorubicin administration to dogs from Example 3. The total mass for each dog was determined. The total inhaled volume of air for the 30 minute drug administration was measured in liters. The aerosol concentration in mg of drug/liter of air (mg/l) was determined from calibration tests done earlier. A total deposition fraction of 60% was calculated (As calculated 30% for the inhaled dose was deposited in the conducting upper airways and peripheral lung while and additional 30% was deposited in the oral-pharyngeal region) based on the measured doxorubicin aerosol particle size and the published literature (see references cited above).

Thus about 25%–30% of the administered doxorubicin was deposited and available to the pulmonary region. Since the drug was administered in its salt form, a correction for the chlorine portion of the molecule was made. As shown in the Table 4 this resulted in an applied dose of 0.51, 0.60, and 0.57 mg/kg to the pulmonary region of dogs 101, 102, and 103 respectively Filter data obtained from analysis of drug deposited on a filter 421 placed in a fourth mask 415 are shown in Table 5 for four different measurements . The drug mass collected on the filter was corrected for the chlorine portion of the doxorubicin salt. Finally, the doxorubicin concentration in the three liters of air drawn into each mask was determined in mg/l. The four figures were averaged to obtain a mean doxorubicin aerosol concentration of 0.218 mg/l.

Table 6 shows data and calculations that verify the figures of Table 4. The dog weight and breath volumes measured for Table 4 are used. However, the mean doxorubicin concentration that was obtained from the filter data shown in Table 5 was used to calculate doxorubicin concentrations. Making calculations with the data as in Table 4, the inhaled dose for each dog was calculated. The inhaled dose was reduced by

TABLE 5

FILTER DATA

| Sample No. | Sample Vol. (liter) | Weight Gain (mg) | Doxorubicin mass (mg) | Total Conc. (mg/l) | Dox. Conc. (mg/l) | Ratio Dox/Total |
|---|---|---|---|---|---|---|
| 1 | 3 | 0.78 × .937 | 0.70 | 0.260 | 0.233 | 0.897 |
| 2 | 3 | 0.72 × .937 | 0.61 | 0.240 | 0.203 | 0.847 |
| 3 | 3 | 0.73 × .937 | 0.62 | 0.243 | 0.207 | 0.849 |
| 4 | 3 | 0.77 × .937 | 0.68 | 0.257 | 0.227 | 0.883 |
| Mean | | | | 0.250 | 0.218 | 0.869 |
| | A | B | C | D | | |

TABLE 6

ANALYTICAL DATA

| Dog No. | Dog Weight (kg) | Total Inhaled Vol. (l) | Aerosol Conc. (mg/l) | Inhaled Dose (mg/kg) | Deposited Dose (mg/kg) | Pulmonary Dose (mg/kg) |
|---|---|---|---|---|---|---|
| 101 | 10.66 | 77.5 | 0.218 | 1.58 | 0.95 | 0.47 |
| 102 | 10.24 | 86.8 | 0.218 | 1.85 | 1.11 | 0.56 |
| 103 | 10.02 | 80.8 | 0.218 | 1.76 | 1.06 | 0.53 |
| | A | B | C | | | |

Surprisingly it was found that free non-encapsulated doxorubicin administered by the pulmonary route was not rapidly cleared from the lung. FIGS. 1, 2 and 3 show examples of the type of results achieved when cytotoxic anticancer drugs were given by inhalation. High efficiency nebulization systems as shown in FIGS. 4 and 5 were used to deliver a large percentage of aerosolized drug to the pulmonary region of the respiratory tract. Doses equal to or greater than those that cause toxicity when given IV, were only moderately absorbed into the blood following pulmonary delivery and caused little to no direct or systemic toxicity after a single exposure at this dose.

As can be seen from FIGS. 1, 2 and 3, the pulmonary route administered doxorubicin achieved a consistently lower level of doxorubicin in systemic blood, with peak blood levels being over an order of magnitude lower following inhalation exposure. The initial concentration of doxorubicin at 2 minutes was about 1.5 orders of magnitude larger when administered IV than by the pulmonary route. Later, after about 4 hours, the systemic doxorubicin level was about six times higher for the IV administered drug. This suggests that free doxorubicin remained in the lung for an extended period of time and slowly passed through the mucosa into systemic circulation. This reduces the systemic toxic effects of the drug and allows its concentration in the lung for more effective treatment of respiratory tract associated neoplasms while reducing overall systemic toxic effects. It is believed that the toxic effects of doxorubicin to tissues outside the lung are as a result of the aforementioned high levels of systemic drug concentration following IV treatment.

Another surprising finding was that doxorubicin administered by the pulmonary route did not produce the severe toxic effects on the respiratory tract (including the oral and nasal-pharyngeal, tracheo-bronchial, and pulmonary regions). As was noted earlier, doxorubicin belongs to the anthracycline class of drugs that are typically very toxic. In particular doxorubicin is one of the most toxic drugs in the class, yet when the dogs in the test were necropsied, no damage to the respiratory tract was observed. It is surprising that the doxorubicin was not toxic to the lung when given by inhalation at clinically relevant doses such as 20 to 60 mg/m$^2$. Unlike 5-FU and Ara-C, and cisplatin, doxorubicin is well known to generate the production of free radicals (Myers et al, 1977) which are notorious for causing pulmonary toxicity (Knight, 1995). It is this property, in fact, which is held responsible for the cardiotoxicity caused by doxorubicin given by the intravenous route (Myers et al, 1977).

In some typical embodiments, to obtain additional benefits of the disclosed invention for treating pulmonary neoplasms and reducing systemic toxicity, it is important that antineoplastic drugs administered in non-encapsulated form by the pulmonary route be absorbed into and remain in the tumor tissue for an extended period of time and diffuse across the lung mucosa in a relatively slow manner. In general, although solubility, charge and shape have an influence, slow diffusion is obtained by drugs having higher molecular weights while faster diffusion is obtained by those having relatively lower molecular weights. Thus drugs such as doxorubicin having a molecular weight of 543.5, have relatively slow rates of diffusion, drugs such as vincristine (MW=825), vinblastine (MW=811), paclitaxel (MW=854), etoposide (MW=589), having higher molecular weights also diffuse slowly. Other drugs having somewhat lower molecular weights such as 9-aminocamptothecin, while diffusing more slowly are still included within the invention. It has been demonstrated that significantly higher tissue concentrations can be achieved in the lung by pulmonary delivery compared to conventional parenteral or oral administration. Further, systemic coverage of micrometasteses can be provided under these conditions, with the benefit of significantly greater doses of drug delivered to the respiratory tract tumor sites and controlled systemic exposure.

Thus in one embodiment of the invention drugs having a molecular weight above 350 are used. In this regard mitomycin-C (MW of about 334) is thus excluded from this embodiment. While molecular weight is not the sole determinant controlling diffusion through the lung it is one of the important factors for selecting compounds useful in the present invention. This lower molecular weight limit is about 64% that of doxorubicin. This will help assure that the limited systemic availability of the drug discussed above is maintained. In further embodiments of the invention the molecular weight of the drugs administered is above 400, 450, and 500 respectively.

In conjunction with the above discussed molecular weights, protein binding of the antineoplastic agents to be delivered by pulmonary administration should also be considered with respect to diffusion through the lung. Higher rates of protein binding will further slow diffusion through the lung mucosa. In this respect 5-FU and Ara-C in addition to having low molecular weights also have relatively low protein binding affinity of 7% and 13% respectively. That is, when placed into a protein-containing solution, only 7% and 13% of these drugs bind to the protein while the remainder is free in solution. In this respect, cisplatin does not bind to tissues, rather at a later stage it is the platinum in the cisplatin that binds to tissues, thus allowing cisplatin to enter systemic circulation as further discussed below. In comparison doxorubicin, vincristine, vinblastine, paclitaxel, etoposide, and 9-amino-camptothecin have rates of protein binding above 50%. Typically protein-binding affinity above 25% is preferred, more preferred is binding above 50%, with protein binding above 75% being most preferred when lung retention is the objective.

In a preferred formulation and method for treating neoplasms of the pulmonary system by inhalation, the diffusion characteristics of the particular drug formulation through the pulmonary tissues are chosen to obtain an efficacious concentration and an efficacious residence time in the tissue to be treated. Doses may be escalated or reduced or given more or less frequently to achieve selected blood levels. Additionally the timing of administration and amount of the formulation is preferably controlled to optimize the therapeutic effects of the administered formulation on the tissue to be treated and/or titrate to a specific blood level.

Diffusion through the pulmonary tissues can additionally be modified by various excipients that can be added to the formulation to slow or accelerate the absorption of drugs into the pulmonary tissues. For example, the drug may be combined with surfactants such as the phospholipids, dimyristoylphosphatidyl choline, and dimyristoylphosphatidyl glycerol. The drugs may also be used in conjunction with bronchodilators that can relax the bronchial airways and allow easier entry of the antineoplastic drug to the lung. Albuterol is an example of the latter with many others known in the art. Further, the drug may complexed with biocompatible polymers, micelle forming structures or cyclodextrins.

Particle size for the aerosolized drug used in the present examples was measured at about 2.0–2.5 $\mu$m with a geometric standard deviation (GSD) of about 1.9–2.0. Typically the particles should have a particle size of from about 1.0–5.0 $\mu$m with a GSD less than about 2.0 for deposition within the central and peripheral compartments of the lung. As noted elsewhere herein particle sizes are selected depending on the site of desired deposition of the drug particles within the respiratory tract.

Aerosols useful in the invention include aqueous vehicles such as water or saline with or without ethanol and may contain preservatives or antimicrobial agents such as benzalkonium chloride, paraben, and the like, and/or stabilizing agents such as polyethyleneglycol.

Powders useful in the invention include formulations of the neat drug or formulations of the drug combined with excipients or carriers such as mannitol, lactose, or other sugars. The powders used herein are effectively suspended in a carrier gas for administration. Alternatively, the powder may be dispersed in a chamber containing a gas or gas mixture which is then inhaled by the patient.

Further, the invention includes controlling deposition patterns and total dose through careful control of patient inspiratory flow and volume. This may be accomplished using the pulmonary devices described herein and similar devices. The inventors have shown by gamma scintigraphy measurements that drug aerosol deposition is maximized and evenly distributed in the peripheral lung when the patient inhales using slow flow rates and inhales to maximum lung volumes followed by brief breath holds. Central lung deposition is favored when faster inspiratory flow rates and lower inspiratory volumes are used. Further, total deposited and regionally deposited doses are significantly changed as a patient's inspiratory patterns change. Therefore, the method of treatment and the use of the delivery devices described herein can be modified to target different regions of the respiratory tract and adjusted too deliver different doses of drug. It is the integration of drug molecular weight, protein binding affinity, formulation, aerosol generation condition, particle sized distribution, interface of aerosol delivery to the patient via the device and the control of the patient's inspiratory patterns that permit targeted and controlled delivery of highly toxic anti-cancer drugs to the respiratory tract with the option to minimize or provide controlled systemic availability of drug.

EXAMPLE 4

The tests for administration of doxorubicin by inhalation referred to in Example 3 were substantially repeated at different dosages using a different drug administration system 500 described below. In the present examples eight dogs were used. The dogs were divided into two dose groups. A first group was the low dose group given a total daily dose of 60 mg/m$^2$ for three days or a total dose of 180 mg/m$^2$. This resulted in a pulmonary deposition of about 90 mg/m$^2$.

A high dose group was administered a dose of 180 mg/m$^2$ daily for three days or a total dose of 540 mg/m$^2$. This resulted in a pulmonary deposition of about 270 mg/m$^2$.

One half of the animals were necropsied after three days of exposure and the remaining dogs necropsied after a three day recovery period.

The purpose of the tests was to identify the maximum tolerated dose of inhaled drug.

For comparison with the results of Examples 2 and 3, one can convert the data from mg/kg to mg/m$^2$ (m$^2$ of body area) by multiplying by 20 (conversion factor for the dog). Thus the exposure of the dogs in Examples 2 and 3 which were the equivalent of a clinical dose (for dogs) was about 20 mg/m$^2$. When one compares these dosages to those of Example 4 (180 mg/m$^2$ and 540 mg/m$^2$) it is apparent that a significantly higher dose of non-encapsulated drug can be delivered to the lung compared to the known art. Although dogs receiving the lower total dose ranges showed few toxic effects, while dogs receiving the higher total doses had pulmonary toxicity, these doses were 9–27 times higher than those generally given clinically to dogs.

While the present examples used active drug doses of doxorubicin of about 20 mg/m$^2$, 180 mg/m$^2$, and 270 mg/m$^2$, effective amounts of the active anticancer drugs can be from very small amounts to those where toxicity to normal tissue becomes a problem. As used herein, effective amounts and pharmaceutically effective amounts of antineoplastic drug deposited or applied to areas needing treatment are dosages that reduce a neoplasm or tumor mass, stop its growth or eliminate it altogether.

Figure 5:
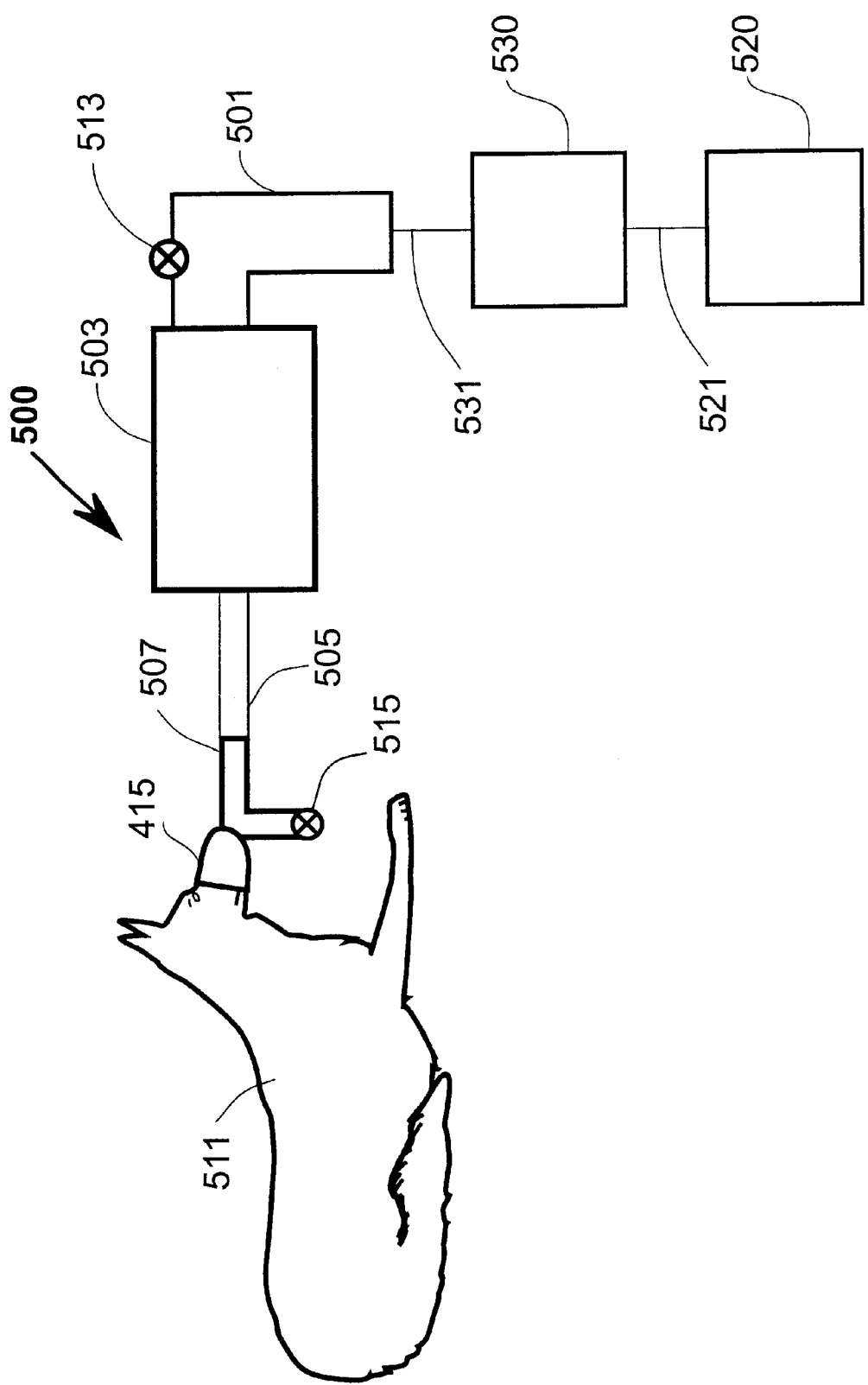
FIG. 5 shows a schematic of the pulmonary delivery apparatus arrangement that was used to administer high doses and multiple doses of drug to dogs by inhalation for Example 4.

Referring now to FIG. 5, the liquid formulation was administered to the dogs by aerosolizing with a nebulizer exposure system 500 comprising a Pari LC Jet Plus™ nebulizer 501. The nebulizer was filled with the solution of drug with which the dogs were to be treated. The output of the nebulizer 501 was pulsed in a series of bursts over time (one pulse every ten seconds). The nebulizer 501 was attached directly to a 460 cc volume plenum 503 and the plenum 503 was connected to a canine mouth only exposure mask 415 via a short piece of anesthesia tubing 505 and Y-fitting 507. The mask 415 was tapered to approximately fit the shape of the dog's snout. There was no bias airflow through the exposure system 500. The test atmosphere was pulled through the exposure system 500 by the inhalation of the dog 511. A one way breathing valve 513 on the top of the nebulizer 501 allowed the dog 511 to draw in room air and pull the air through the system 500. The air entrained and transported the aerosolized drug through the plenum 503, tubing 505, Y-fitting 507, and mask 415 to the dog 511. A one way valve 515 connected to the Y-fitting 507 allowed the dog 511 to exhale and the exhaled air exited the system. An air supply 520 provided a flow of air to controller 530 via line 521. Air flow to the nebulizer was controlled by controller 530 and supplied to the nebulizer via line 531.

Figure 6:
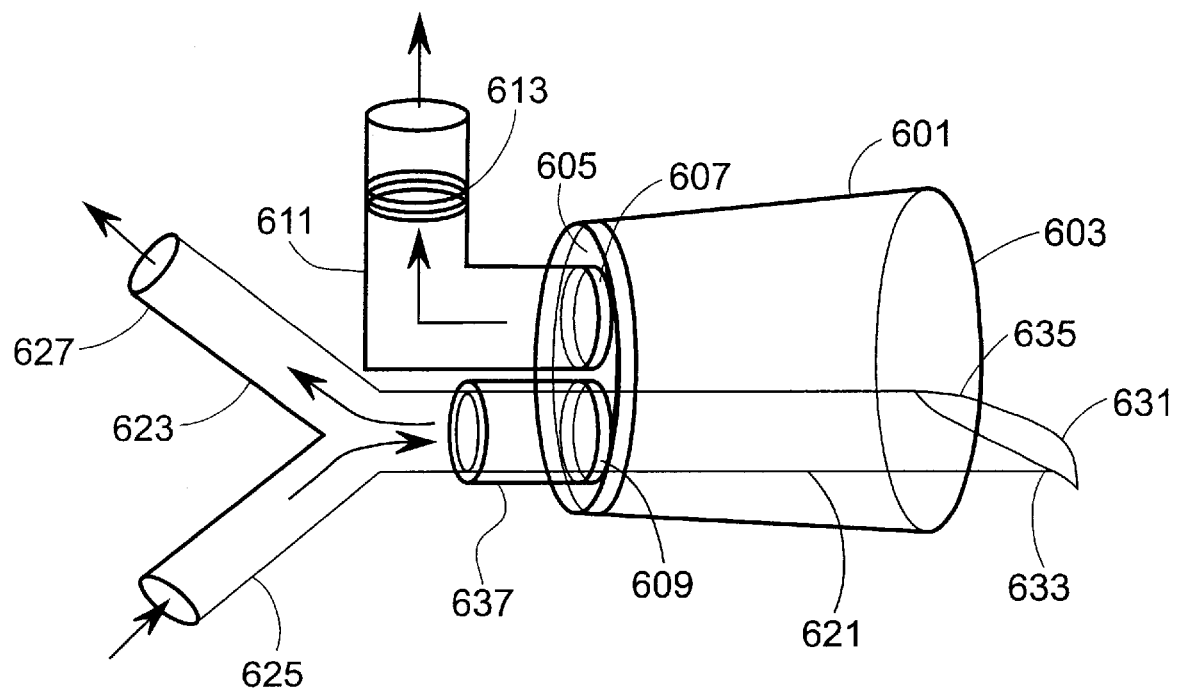
FIG. 6 shows a schematic drawing of details of a mask useful for administering drugs by inhalation to a mammal such as a dog.

Referring now to FIG. 6, details of mask 415 are shown. Means for enclosing the mouth and nose are of flexible material and are preferably held on by straps such as Velcro™ straps or belts. Means for enclosing 601 has one end 603 for inserting the nose and mouth of the dog while the other end 605 has two openings 607,609 for attachment of nose outlet tube 611. Nose outlet tube 611 has a one way valve 613 that allows the dog to exhale but not inhale through the its nose. Mouth tube 621 is inserted and attached to opening 609 and lies within the means for enclosing 601. An optional Y-connector 623 may be attached and used with mouth tube 621 for providing and receiving inhaled and exhaled gases. Air is generally inhaled through leg 625 of the Y-connector 623. The air passes through the mouth tube 621 and out the inner opening 631 into the respiratory system of the dog. Inner opening 631 is cut at an angle with its lower portion 633 extending further into the mouth of the dog than the upper portion 635. Lower portion 633 functions to depress the tongue of the dog and allow more efficient flow of air and aerosol into the dog. When the dog is wearing mask 415 it can only breathe in through its mouth using the mouth tube 621. Means for enclosing 601 effectively seals the dog's mouth and nose from outside air. The use of a nose outlet tube 611 has been found to greatly ease the dogs wearing of the mask. Air exhaled through the mouth exits mouth tube 621 and passes into optionally attached Y-connector or to another tube not shown. Air exits Y connector 623 via outlet tube 627. If desired the Y-connector 623 or other outer tube (e.g. straight tubing) may be made of one piece and simply pass into the enclosing means 601 or may be of separate pieces that fit together. In either case an adapter 637 may be used to hold the mouth tube 621 and or other tubing to which it is connected.

A general device for administering aerosols to a patient includes an inhalation mask for administering aerosols to the including means for enclosing the mouth and nose of the patient, having an open end and a closed end, the open end adapted for placing over the mouth and nose of the patient; upper and lower holes in the closed end adapted for insertion of a nose outlet tube and a mouth inhalation tube; the nose outlet tube attached to the upper hole, adapted to accept exhaled breath from the nose of the patient; a one way valve in the nose tube adapted to allow exhalation but not inhalation; the mouth inhalation tube having an outer and an inner end, partially inserted through the lower hole, the inner end continuing to end at the rear of the patients mouth, the inhalation tube end cut at an angle so that the lower portion extends further into the patients mouth than the upper portion and adapted to fit the curvature of the rear of the mouth; and a y-adapter attached to the outer end of the mouth inhalation tube.

Pulmonary administration by inhalation may be accomplished by means of producing liquid or powdered aerosols, for example, by the devices disclosed herein or by using any of various devices known in the art. (see e.g. Newman, S. P., 1984, in Aerosols and the Lung, Clarke and Davia (Eds.), Butterworths, London, England, pp. 197–224; PCT Publication No. WO 92/16192 dated Oct. 1, 1992; PCT Publication No. WO 91/08760 dated Jun. 27, 1991; NTIS Patent Application 7-504-047 filed Apr. 3, 1990 by Roosdorp and Crystal) including but not limited to nebulizers, metered dose inhalers, and powder inhalers. Various delivery devices are commercially available and can be employed, e.g. Ultravent nebulizer (Mallinckrodt, Inc, St. Louis, Mo.); Acorn II nebulizer (Marquest Medical Products, Englewood, Colo.); Ventolin metered dose inhalers (Glaxo Inc., Research Triangle Park, N.C.); Spinhaler powder inhaler (Fisons Corp., Bedford, Mass.) or Turbohaler (Astra). Such devices typically entail the use of formulations suitable for dispensing from such a device, in which a propellant material may be present. Ultrasonic nebulizers may also be used.

Nebulizer devices such as those in Greenspan et al U.S. Pat. Nos. 5,511,726 and 5,115,971 are useful in the invention. These devices use electrohydrodynamic forces to produce a finely divided aerosol having uniformly sized droplets by electrical atomization. While the Greenspan devices use piezoelectric materials to generate electrical power any power source is acceptable to produce the electrohydrodynamic forces for nebulization.

A nebulizer may be used to produce aerosol particles, or any of various physiologically inert gases may be used as an aerosolizing agent. Other components such as physiologically acceptable surfactants (e.g. glycerides), excipients (e.g. lactose), carriers (e.g. water, alcohol), and diluents may also be included.

As will be understood by those skilled in the art of delivering pharmaceuticals by the pulmonary route, a major criteria for the selection of a particular device for producing an aerosol is the size of the resultant aerosol particles. Smaller particles are needed if the drug particles are mainly or only intended to be delivered to the peripheral lung, i.e. the alveoli (e.g. 0.1–3 $\mu$m), while larger drug particles are needed (e.g. 3–10 $\mu$m) if delivery is only or mainly to the central pulmonary system such as the upper bronchi. Impact of particle sizes on the site of deposition within the respiratory tract is generally known to those skilled in the art. See for example the discussions and figures in the articles by Cuddihy et al (Aerosol Science; Vol. 4; 1973, pp 35–45) (FIGS. 6, 7, and 8 of the article) and The Task Group on Lung Dynamics (FIG. 11 and 14 of the article). As a result primary cancers in the naso-pharyngial or oral-pharyngeal regions and upper tracheo-bronchial regions, often referred to as cancers of the head and neck, are treatable with the present invention. The major metastatic sites (lung and upper respiratory tract) are also readily treated with this invention simultaneously, unlike current methods of treatment.

Figure 7:
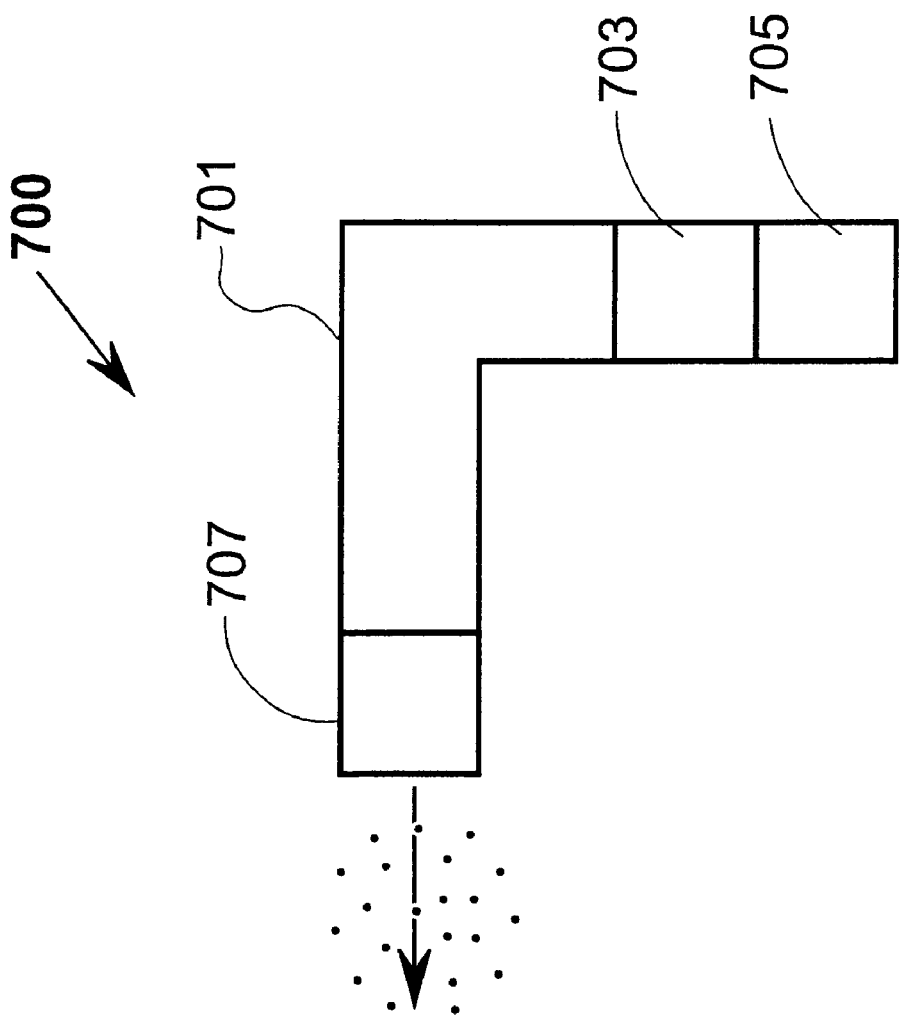
FIG. 7 shows a schematic drawing of a portable device for administration of anticancer drugs according to the invention.

Referring now to FIG. 7, there is disclosed a nebulizer apparatus 700 that is preferably portable for administration of drug to a patient in need of therapy. The nebulizer apparatus 700 is used in combination with the highly toxic drugs of the present invention and with drugs having properties adapted for optimum treatment of neoplasms as discussed elsewhere herein. FIG. 7 is a schematic of a nebulizer combination according to the present invention. Nebulizer 701 may be any nebulizer as described earlier herein that is able to produce the particle sizes needed for treatment. In combination with nebulizer 701 there is provided a highly toxic drug formulation 703 for treatment of neoplasms as disclosed herein. An air supply 705 is provided either as a tank of compressed gas or as a motorized pump or fan for moving air from the room. An optional mouthpiece 707 may be used where it is necessary to provide sealed contact between the nebulizer and the patient. Optionally the mouthpiece 707 may be molded as part of nebulizer 701. Power for use of the nebulizer apparatus 700 may come from the compressed gas from hand manipulation by the user or administrator or by batteries or electrical power not shown but well known by those skilled in the art.

To control environmental contamination resulting from use of a nebulizer, the patient may be placed in a well-ventilated area with exhaust air filtered to remove antineoplastic drug that escapes from the device.

EXAMPLES 5 to 11

Examples 5F to 11F show inhalation feasibility and proof of concept tests and Examples 5R to 10R show dose escalation range tests with: vesicant antineoplastic drugs including doxorubicin, paclitaxel, vincristine, vinorelbine; nonvesicant drugs including etoposide, and 9-aminocampothecin (9-AC) and carboplatin. The drugs were delivered to the pulmonary system via aerosol at a particle size of about 2 to about 3 $\mu$m. The drugs were delivered in water or other vehicles appropriate for the drug as is known in the art and as exemplified herein.

Table 7 illustrates the dosage schedule for the range-finding studies. A minimum of 7–14 days separated each escalating dose. No range finding tests, only feasibility tests, were performed for mitomycin-C and 9-AC. No feasibility tests, only dose range-finding tests, were performed for vinorelbine. It is important to note that the doses listed in Table 7 are the pulmonary deposited doses not the total doses administered.

The results of the feasibility and dose escalation studies are summarized in Tables 7 to 11.

TABLE 7

Escalating Dose Regimen for Range-Finding Studies
Mean Pulmonary Deposited Dose

| Example No. | Test Drug | 1st Dose (mg) | 2nd Dose (mg) | 3rd Dose (mg) | 4th Dose (mg) | 5th Dose (mg) | 6th Dose (mg) |
|---|---|---|---|---|---|---|---|
| 5R | Paclitaxel | 30 | 35 | 40 | 40 | 60 | — |
| 6R | Doxorubicin | 12 | 15 | 15 | 15 | 18 | — |
| 7R | Vincristine | 0.55 | 0.55 | 0.70 | 0.70 | 1.1 | 1.5 |
| 8R | Vinorelbine | 6 | 10 | 10 | 15 | 15 | — |
| 9R | Etoposide | 25 | 30 | 45 | 55 | 40 | 80 |
| 10R | 9-AC | — | — | — | — | — | |
| 11R | Carboplatin | 30 | — | — | — | — | |

Notes:
A minimum of 7–14 days separated each escalating dose.
Animals necropsied after last dosing Animals used in Examples 5 to 11 were adult beagle dogs. For the feasibility studies, the dogs were initially given a single intravenous (IV) dose of antineoplastic drug. This dose was given to allow a comparison of how much drug was absorbed into the blood after inhalation compared to IV delivery. The IV dose given was typically the usual human clinical dose that had been scaled down for the dogs based on differences in body mass, or the maximum tolerated dose in the dog, whichever is greater. An average human having a weight of 70 kg is considered to have a weight to body surface ratio of 37 kg/m$^2$ and a lung surface area of 70-100 m$^2$ of lung surface area. The average dog used in the tests was considered to have a weight of 10 kg corresponding and a weight to body surface ratio of 20 kg/m$^2$ and a lung surface area of 40–50 m$^2$ lung surface area (CRC Handbook of Toxicology, 1995, CRC Press Inc.). The single IV dose was used to quantify the plasma kinetics. With most of the cytotoxic agents treated, the single IV dose resulted in a predictable mild decrease in white blood cell counts, with no other measurable toxicities.

After the initial IV and before the inhalation feasibility tests, the dogs were allowed a washout period of at least seven days (until the dogs returned to normal conditions) before they were treated with inhaled antineoplastic drugs. In the inhalation feasibility tests the dogs were generally exposed to a dose of inhaled antineoplastic drug in aerosol form once per day for three consecutive days (except as noted in Tables 8 to 11) and necropsied one day following the last dose with the plasma kinetics characterized after the first and third exposures. With the exception of cisplatin and the high dose of doxorubicin, which caused toxicity to the respiratory tract, the drugs did not exhibit any significant pulmonary toxicity in these repeated exposure inhalation feasibility studies. In the feasibility tests the dogs used the same mask and apparatus used for the earlier examples. In the dose range-finding tests, in order to control the deposited dose, the dogs were fitted with an endo-tracheal tube and the drug administered as an aerosol directly from the endo-tracheal tube. This latter procedure made it easier to control the pulmonary deposited dose since the aerosol was released directly into the pulmonary air passages assuring deep deposition of the drug in the lung. Also use of the endo-tracheal tube made it possible to do the tests in a shorter time since the dogs needed a four to six week training period to properly acclimate to and use the masks. The calculated deposited doses obtained herein were verified experimentally by pulmonary scintigraphy tests in dogs.

EXAMPLES 5F and 5R

Referring now to Table 8, this table shows the details of the feasibility test of paclitaxel. Initially the dogs were administered 120 mg/m$^2$ of paclitaxel by IV. After the washout period the dogs were administered a total deposited dose of 120 mg/m$^2$ of paclitaxel, by inhalation, three times for a total deposited dose of 360 mg/m$^2$. This administered dose resulted in a pulmonary deposited dose of about 27 mg each time or a total pulmonary dose of about 81 mg. This represents a total pulmonary deposited dose of about 2.1 mg/m$^2$ of lung surface area. The dosages were calculated as follows: the dose of 120 mg/m$^2$ was divided by 20 kg/m$^2$ to yield a 6 mg/kg dose that was multiplied by 10 kg for the average dog to yield about 60 mg of drug. Since the dogs were using the masks for drug administration, one half or about 30 mg of drug was considered deposited in the deep lung. Since the drug was administered three times the total drug exposure was about 90 mg. The 90 mg of drug was divided by 40 to yield a total dose to the lung of about 2.25 mg/m$^2$ lung surface area.

The clinical condition of the dogs was normal. Clinical pathology profiles were normal with only mildly reduced white blood cell counts. The histopathology showed bone marrow and lymphoid depletion, GI villous atrophy and congestion and laryngeal inflammation. These changes indicated that some significant fraction of the deposited drug was absorbed systemically. There was no respiratory tract toxicity found. Bioavailability of the paclitaxel was found to be low to moderate based on plasma kinetic evaluations. The low to moderate bioavailability indicates that most of the paclitaxel remained in the lungs and did not rapidly enter systemic circulation in large amounts. Therefore, given the lack of significant direct respiratory tact toxicity, the probable dose limiting toxicity is considered to be myelosuppression and/or GI toxicity. Thus factors extrinsic to the lung are expected to limit dosages provided by the pulmonary route.

Referring again to Tables 7 and 8, in the range-finding tests 60 to 120 mg/m$^2$ of paclitaxel were administered at weekly intervals for five weeks. The amount of pulmonary deposited dose ranged from about 30 to about 60 mg. This range corresponded to about 0.75 to about 1.50 mg/m$^2$ lung surface area. The clinical conditions of these dogs were normal, with clinical pathology changes limited to moderate white blood cell count reduction. The histopathology showed thoracic and mesenteric lymphoid depletion along with GI inflammation and ulceration. The histopathology reflects that normally found in IV administration of paclitaxel particularly GI inflammation and ulceration which is probably associated with systemically administered paclitaxel. Respiratory tract toxicity indicated minimal pulmonary interstitial inflammation. Systemic bioavailability was proportional to dose. The probable dose limiting toxicity is myelosuppression and GI toxicity, and not pulmonary toxicity.

dose group, but were considered survivable at the lower dose, based on the clinical condition of the animals. Despite these higher doses, there were no clinical pathology changes indicative of doxorubicin induced myelosuppression. There was microscopic evidence of lymphoid depletion in the regional lymph nodes of the respiratory and gastrointestinal

TABLE 8

Paclitaxel
Summary Results of Dog Feasibility and Dose Range-Finding Studies

| Chemo-therapy | IV dose | Inhalation Dose | Pulmonary Deposited Dose | Clinical Condition | Clinical Pathology | Histopathology | Respiratory Tract Toxicity | Bioavailability | Probable Dose-Limiting Toxicity |
|---|---|---|---|---|---|---|---|---|---|
| Example 5F Paclitaxel Feasibility | 120 mg/m$^2$ | 120 mg/m$^2$ × 3 (360 mg/m$^2$ total) | 30 mg × 3 doses | Normal | ↓ WBC | Bone marrow & lymphoid depletion GI villous Atrophy & congestion Laryngeal inflammation | None | Low-moderate | Myelosuppression GI toxicity |
| Example 5R Paclitaxel Dose Range-Finding | NA | 60–120 mg/m$^2$ (5 wkly Rx) | 30–60 mg per dose | Normal | ↓↓ WBC | Thoracic and mesenteric lymphoid depletion GI inflammation and ulceration | Minimal pulmonary interstitial inflammation | Proportional to dose | Myelosuppression GI toxicity |

\* - Divide the pulmonary deposited dose in mg by 40 to get the pulmonary deposited dose in mg/m$^2$ of lung surface area.
WBC - white blood cell count

EXAMPLES 6F and 6R

Referring now to Table 9, 20 mg of doxorubicin were initially administered by IV. After the washout period three sets of inhalation feasibility tests were made. In the first, a single dose of 20 mg/m$^2$ of doxorubicin was administered that gave about a 10 mg body dose, a pulmonary deposited dose of about 5 mg or about 0.125 mg/m$^2$ lung surface area. No changes were noted in the animal from this dose. A second set of moderate inhalation dosages of about 40 mg/m$^2$ of doxorubicin (about 10 mg deposited within the lung) was administered three times a day for three consecutive days. Total cumulative dose administered was 120 mg/m$^2$ corresponding to a about a 60 mg body dose, and a total pulmonary deposited dose of about 30 mg (or about 0.75 mg/m$^2$ of lung surface area). A third set of high inhalation dosages of 120 mg/m$^2$ of doxorubicin was administered three times per day over a three day period for a total dose of 360 mg/m$^2$ corresponding to a 180 mg body dose, a total pulmonary deposited dose of about 90 mg or about 2.25 mg/m$^2$ of lung surface area. One half of the low dose group dogs was necropsied the day after the final exposure and the remaining half was necropsied four days later. All high dose dogs were necropsied the day after the final exposure.

Exposure to these extremely high doses resulted in the death of one high dose group dog after three days of exposure with the remaining three dogs euthanized in moderately debilitated to moribund conditions. This dose intensive treatment caused pulmonary edema, a sequela of microscopically recognizable degeneration, necrosis and inflammation of epithelial surfaces lining the bronchials and larynx and the mucosal surfaces of the nose and lips. These lesions were life threatening and more severe in the high tracts suggestive of regional drainage of free doxorubicin to the draining lymph nodes of the thoracic and GI systems. WBC values actually increased in the high dose group, a change associated with the inflammatory response observed in the respiratory tract. There were no other clinical pathology changes of note other than increased serum alkaline phosphatase in the high dose group, a nonspecific change, due likely to respiratory tract tissue damage.

Generally, changes noted at the moderate and high dosages were edema, increased white blood cell count and increased respiratory rate. Histopathology revealed thoracic and GI lymphoid depletion for the moderate and higher doses, respectively. Respiratory tract toxicity including airway epithelial degeneration and moderate to severe inflammation was noted at the increased dosages. Bioavailability was low to moderate indicating an absorption rate limiting process in movement of the drug into the systemic circulation. The probable dose limiting toxicity of doxorubicin is expected to be respiratory tract toxicity rather than a systemic toxicity.

In addition, a dose escalation study was conducted on a weekly exposure schedule. Initial doses of 12 mg deposited were delivered via endotracheal tube to the lungs, with a 5$^{th}$ weekly dose of 18 mg deposited within the lungs. This provided a total body dose of 24 to 36 mg/m$^2$. The results of this repeated dose trial were similar in character (but not in severity) to the higher dose tests. Animals survived this treatment regimen with minimal clinical evidence of toxicity and no evidence of systemic changes. Histologically, there was no evidence of respiratory tract epithelial degeneration and inflammation.

TABLE 9

Doxorubicin
Summary Results of Dog Feasibility and Dose Range-Finding Studies

| Chemo-therapy | IV dose | Inhalation Dose | Pulmonary Deposited Dose* | Clinical Condition | Clinical Pathology | Histopathology | Respiratory Tract Toxicity | Bioavailability | Probable Dose-Limiting Toxicity |
|---|---|---|---|---|---|---|---|---|---|
| Example 6F Doxorubicin Feasibility | 20 mg/m$^2$ | 20 mg/m$^2$ × 1 | 5 mg | No change | No change | No change | No change | Low-moderate (absorption rate limited) | Respiratory tract toxicity |
| | | 40 mg/m$^2$ × 3 doses (120 mg/m$^2$ total) | 10 mg × 3 doses | Mild-moderate pulmonary edema ↑IRR | ↑ WBC | Thoracic & GI Lymphoid depletion | Airway epithelial degeneration | | |
| | | 120 mg/m$^2$ × 3 doses (360 mg/m$^2$ total) | 30 mg × 3 doses | Marked edema ↑↑IRR | ↑↑ WBC | Thoracic & GI Lymphoid depletion | Moderate-severe inflammation | | |
| Example 6R Doxorubicin Dose Range-Finding | N/A | 24–36 mg/m$^2$ (5 wkly Rx) | 12–18 mg per dose | ↑IRR Mild transient pulmonary edema | ↓ WBC | Mild-moderate thoracic and mesenteric lymphoid depletion | Mild-moderate degeneration of airway epithelium Mild-moderate interstitial inflam. | Low-moderate | Respiratory tract toxicity |

↑ - Increase
↓ - Decrease
IRR - increased respiratory rate
WBC - white blood cells
*Divide the pulmonary deposited dose in mg by 40 to get the pulmonary deposited dose in mg/m$^2$ of lung surface area.

Plasma levels of doxorubicin were dose dependent and exhibited clear evidence of drug accumulation, including daily increases in Cmax (maximum concentration in blood) and steady state-like profiles, suggesting there was a rate limited absorption from the lung into the blood with significant accumulation of doxorubicin in the lungs following each additional exposure given at a frequency of daily intervals. This accumulation was considered likely responsible for the tissue damage observed.

Referring again to Tables 7 and 9, an inhalation dose range of 20–40 mg/m$^2$ was administered in five weekly doses that resulted in a body exposure of about 10 mg to about 20 mg, a pulmonary deposited dose range of about 10 to about 20 mg or a range of about 0.25 mg/m$^2$ to about 0.5 mg/m$^2$ lung surface area. The clinical condition included increased respiratory rate and mild transient pulmonary edema. A decrease in white blood cell count was noted for the higher dosages. Histopathology revealed mild to moderate thoracic and mesenteric lymphoid depletion. Respiratory tract toxicity noted was mild to moderate degeneration of airway epithelium. A mild to moderate to marked interstitial inflammation was noted with some limited fibrosis. Bioavailability was noted to be low to moderate with absorption being rate limited. The probable dose limiting toxicity appears again to be respiratory tract toxicity.

EXAMPLE 7F and 7R

Referring now to Table 10, 1.4 mg of vincristine was initially administered by IV. After the washout period one inhalation feasibility test was made. The vincristine was formulated in a 50% water/ 50% ethanol vehicle. A single dose of 2.8 mg/m$^2$ of vincristine was administered that gave about a 1.8 mg body dose, a pulmonary deposited dose of about 0.9 mg or about 2.25 mg/m$^2$ lung surface area. No changes were noted in the animal from this dose.

TABLE 10

Vincristine & Vinorelbine
Summary Results of Dog Feasibility and Dose Range-Finding Studies

| Chemo-therapy | IV dose | Inhalation Dose | Pulmonary Deposited Dose | Clinical Condition | Clinical Pathology | Histopathology | Respiratory Tract Toxicity | Bioavailability | Probable Dose-Limiting Toxicity |
|---|---|---|---|---|---|---|---|---|---|
| Example 7F Vincristine Feasibility | 1.4 mg/m$^2$ | 2.8 mg/m$^2$ × 1 | 0.7 mg | Normal | Normal | No change | No change | Undetermined | Undetermined |
| Example 7R Vincristine Dose Range- | N/A | 1.1–3.0 mg/m$^2$ (6 wkly Rx) | 0.55–1.5 mg/dose | Normal | ↓ WBC | Minimal-mild bone marrow and lymphoid | Minimal interstitial inflammation | Undetermined | Myelosuppression |

TABLE 10-continued

Vincristine & Vinorelbine
Summary Results of Dog Feasibility and Dose Range-Finding Studies

| Chemo-therapy | IV dose | Inhalation Dose | Pulmonary Deposited Dose | Clinical Condition | Clinical Pathology | Histopathology | Respiratory Tract Toxicity | Bioavailability | Probable Dose-Limiting Toxicity |
|---|---|---|---|---|---|---|---|---|---|
| Finding Example 7R Vinorelbine Dose Range-Finding | N/A | 12–30 mg/m² (5 wkly Rx) | 6–15 mg per dose | Normal | ↓ WBC | depletion Bone marrow and lymphoid depletion | Minimal pulmonary and airway inflam. | Undetermined | Myelo-suppression |

↑ - Increase
↓ - decrease
IRR - increased respiratory rate
WBC - white blood cell
\* - Divide the pulmonary deposited dose in mg by 40 to get the pulmonary deposited dose in mg/m² of lung surface area.

Referring now to Tables 7 and 10, range finding tests of inhaled vincristine were made in the range of 0.5 to 1.5 mg of pulmonary deposited vincristine administered in six weekly doses. Therefore the amount of pulmonary deposited dose ranged from about 12.5–37.5 µg/m² lung surface area. This corresponded to a total body dose of 50–150 µg/kg or 1.0-3.0 mg/m² of body surface area. This dose range is near and generally above typical dose ranges for vincristine given IV. But in the examples given here, the entire dose was administered to the lungs. Vincristine is a potent drug and causes significant myelosuppression and neurotoxicity at doses above 1.0 mg/m² given systemically. The results of the pilot inhalation studies showed the drug was well tolerated at all doses delivered by pulmonary administration with little to no evidence of respiratory tract toxicity with mild lymphoid depletion/myelosuppression only occurring at the highest doses given (2.0–3.0 mg/m²).

EXAMPLE 8R

Vinorelbine, which is also a vinca alkaloid was evaluated in a repeated exposure pilot tests. Compared to vincristine, vinorelbine was approximately 5–10 times less potent in producing toxicity, but produced similar types of changes. Vinorelbine delivered by pulmonary administration directly into the lungs of dogs by endotracheal tube, on a weekly basis (for 5 weeks) at escalating doses was well tolerated. A dose of 6 mg deposited in the lung was initially selected and escalated to 15 mg deposited within the lung. This represented a lung surface exposure of ~0.15–0.375 mg/m² of lung surface area and total body doses of 12–30 mg/m². This treatment regimen produced very minimal effects within the respiratory tract, characterized principally by slight inflammation. At the higher dose levels, inhaled vinorelbine produced sufficient blood levels to cause mild to moderate myelosuppression and lymphoid depletion, both of which were reversible and of a severity, which was not life-threatening.

EXAMPLES 9F and 9R

An additional proof of concept, pilot inhalation tests involved etoposide. Etoposide is a cytotoxic drug, representative of a class of drugs known as topoisomerase II inhibitors. Given orally or IV, etoposide causes typical cytotoxic systemic toxicity, including myelosuppression, severe GI toxicity and alopecia. Etoposide is a highly insoluble drug and therefore difficult to formulate. The vehicle used clinically also causes adverse effects, predominantly anaphylactic type reactions.

In this invention, etoposide was reformulated in a novel vehicle, dimethylacetamide (DMA) which does not cause anaphylactic reactions. While DMA cannot be used for IV administration due to systemic toxicity, it was shown to be a safe delivery vehicle for the pulmonary route of delivery. The etoposide was delivered in a 100% DMA vehicle. This formulation allowed the formation of the appropriate particle sizes. In these tests, escalating doses of etoposide were given to dogs on a weekly schedule. The initial dose used was 25 mg of etoposide deposited in the pulmonary region with a $6^{th}$ and final dose delivered of 80 mg deposited within the pulmonary region. This equated to a dose range of 50–160 mg/m² of body surface area. This treatment regimen caused no systemic toxicity and only minimal inflammation of the lung and no overt damage of the respiratory tract. In addition, there was good evidence of lymphoid depletion of the thoracic lymph nodes, in the absence of systemic changes, indicating that the drug was draining directly through the regional lymph system. This would provide additional regional therapeutic effectiveness in dealing with metastatic cells.

Figure 2:
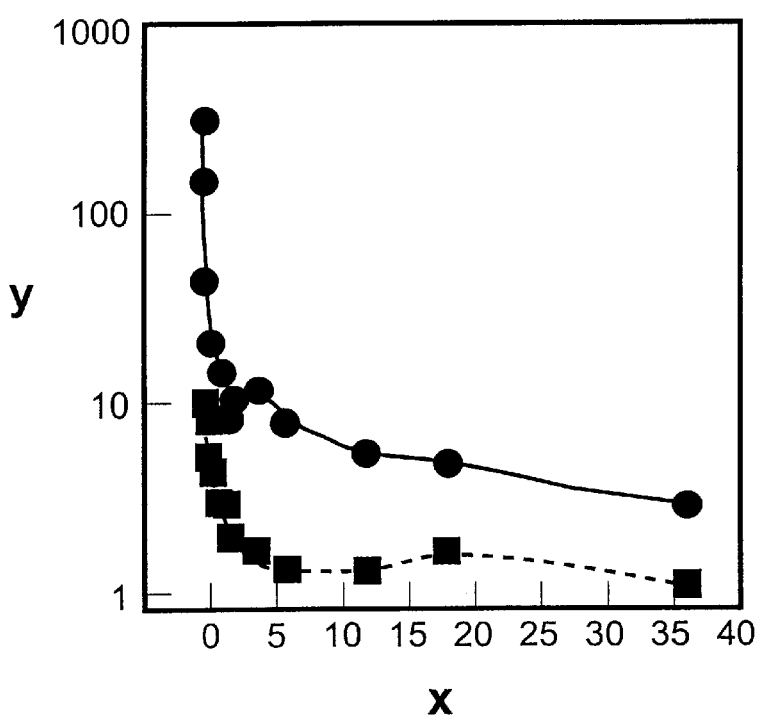
FIG. 2 shows the plasma drug concentration time profile for dog #102 having doxorubicin administered intravenously (IV) (circles) and by the pulmonary inhalation route (IH) (squares). The vertical Y scale is the concentration of drug in the circulatory system in ng/ml and the horizontal X scale is time after treatment in hours.
Figure 3:
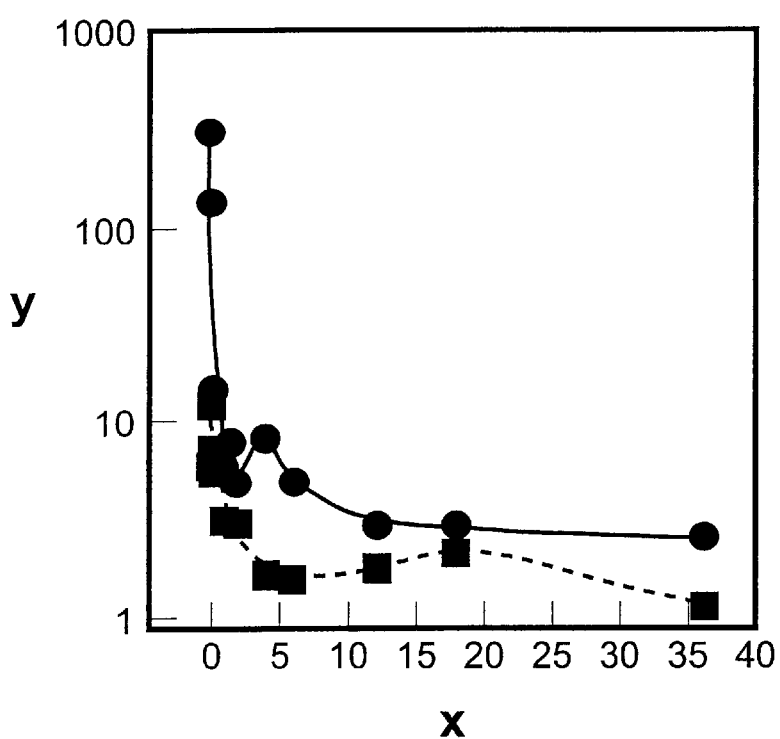
FIG. 3 shows the plasma drug concentration time profile for dog #103 having doxorubicin administered intravenously (IV) (circles) and by the pulmonary inhalation route (IH) (squares). The vertical Y scale is the concentration of drug in the circulatory system in ng/ml and the horizontal X scale is time after treatment in hours.

An additional pharmacokinetic test of inhaled etoposide showed the drug had moderately good bioavailability. A single inhaled total deposited dose of 260 mg/m² (about 65 mg of drug deposited in the pulmonary region) produced blood levels of etoposide similar to an IV dose of 50 mg/m² (see FIGS. 1–3). In other words, to reach similar blood concentrations approximately 5× more drug was given by inhalation, a dose which caused neither respiratory tract nor systemic toxicity.

EXAMPLE 10F

Additional proof of concept inhalation studies involved the cytotoxic drug 9-aminocamptothecin (9-AC) which is within the drug class known as camptothecins. Like etoposide, 9-AC is insoluble and difficult to formulate. Supporting the concept and claims of this invention, the inventors generated aerosols of 9-AC formulated as a microsuspension in an aqueous vehicle (100% water).

These aerosols were delivered to dogs at daily doses of 40 mg/m² body surface area (10 mg of drug deposited within the pulmonary region) for 3 consecutive days. Inhalation treatment produced lower drug plasma levels than an IV dose of 10 mg/m². The daily inhalation dose was 4 times greater than the IV dose and the total cumulative 3 day inhalation dose was 12 times greater than the single IV dose given (which causes mild systemic toxicity). Despite the significantly greater doses given by inhalation, there were no measurable toxic effects (neither local effects within the respiratory tract nor systemic changes). Results from these tests supported the concept of improved overall safety and dose-intensification within the respiratory tract and also demonstrated the concept with aerosolized microsuspensions of chemotherapeutic drugs.

EXAMPLE 11F

In addition, this feasibility trial was extended to examine another platinum-containing chemotherapeutic, carboplatin. The usual clinical formulation using water was used. Carboplatin is generally considered less toxic than cisplatin at comparable doses, and this appeared consistent with the results seen when the two agents were delivered by inhalation. Inhaled doses of up to 30 mg carboplatin deposited via endotracheal tube into the lungs of dogs (60 mg/m² total body dose) caused no evidence of either direct respiratory tract or systemic toxicity.

of the lung progressed even while the lung tumors were stabilized. Thus, the results demonstrated that inhalational chemotherapy was effective in the local treatment of lung cancer in the dog.

TABLE 12

Summary of Preliminary Clinical Results in Dogs

| Dog Type Ex. and Age | Diagnosis | Inhalation Treatment* | Time of Trial | Results |
|---|---|---|---|---|
| 12 Afghan 10 years old | Advanced lung carcinoma | Dox 5 mg, × 1 | 1 week | PD extra-pulmonary |
| 13 Cocker Spaniel 10–12 years old | Lung metastasis from excised melanoma | Dox 5 mg, × 2 Vincristine 0.5 mg, once | 2 mo. | SD lung, died PD extra-pulmonary, died |

TABLE 11

Etoposide, & 9-Aminocampothecin (9-AC)
Summary Results of Dog Feasibility and Dose Range-Finding Studies

| Chemo-therapy | IV dose | Inhalation Dose | Pulmonary Deposited Dose* | Clinical Condition | Clinical Pathology | Histopathology | Respiratory Tract Toxicity | Bioavailability | Probable Dose-Limiting Toxicity |
|---|---|---|---|---|---|---|---|---|---|
| Example 9F Etoposide Feasibility | 50 mg/m² | 260 mg/m² × 3 (780 mg/m² total dose) | 65 mg × 3 doses | Normal | No change | Mild thoracic lymphoid depletion | None | Moderate | Undetermined |
| Example 9R Etoposide Dose Range-Finding | N/A | 50–160 mg/m² (6 wkly Rx) | 25–80 mg dose | Normal | No change | Mild-moderate thoracic lymphoid depletion | Mild interstitial inflammation | Moderate | Undetermined |
| Example 10F 9-AC Feasibility | 10 mg/m² | 40 mg/m² × 3 (120 mg/m² total) | 10 mg × 3 doses | Normal | No change | Minimal lymphoid depletion | Minimal interstitial inflammation | Moderate-high | Undetermined |

*Divide the pulmonary deposited dose in mg by 40 to get the pulmonary deposited dose in mg/m² of lung surface area.

EXAMPLES 12 to 20

These examples illustrate results of clinical treatment of dogs having end stage lung cancer where other treatments have failed. For treatment, the dogs were anaesthetized and the inhalation treatment was through an endotracheal tube.

This preliminary trial was performed to determine whether the inhalation chemotherapy treatment could be successfully used in animals with lung tumors. Initially, nine dogs with neoplastic lung disease were studied. Three different drugs were used- doxorubicin, vincristine, cyclophosphamide, cisplatin, and paclitaxel at the doses and schedules summarized in Table 12.

One 16 year old mixed breed dog had no evidence of tumor in the lung following excision of a primary lung tumor, but did have evidence of metastases in the hilar lymph nodes, a sign that metastases would soon appear in the lung. However, the results showed that no metastases developed in the lung for four months during which time the dog received four treatments of inhaled doxorubicin. In six other dogs, there were metastases in the lung and in each of these, the inhaled chemotherapy stopped the growth of the metastases, i.e. there was stable disease (or SD). In two dogs inhalational chemotherapy was not effective and there was progressive disease (or PD). Since no chemotherapy was given to these dogs by the intravenous route, tumors outside TABLE 12-continued Summary of Preliminary Clinical Results in Dogs

| Dog Type Ex. and Age | Diagnosis | Inhalation Treatment* | Time of Trial | Results |
|---|---|---|---|---|
| 14 Beagle 7 years old | Thyroid carcinoma with lung metastasis | Dox 5 mg, × 4 | 4 mo. | SD lung PD thyroid & extra-pulmonary, died |
| 15 Labrador 8 years old | Thyroid carcinoma with lung metastasis | Dox 5 mg, × 2 | 2 mo. | SD lung PD thyroid & brain metastasis, died |
| 16 Mixed Breed 16 years old | Excised primary, positive hilar lymph nodes | Dox 5 mg, × 4 | 4 mo. | No lung metastasis Death (CNS metastasis) |
| 17 Rottweiler 3 years old | Excised distal osteo-sarcoma, lung nodule | Dox 7 mg, × 2 Cisplatin 15 mg, × 1 | 1 mo. | PD lung Further Rx declined |
| 18 Mixed | Lung | (Dox 5 mg + | 2-½ mo. | SD lung |

TABLE 12-continued

Summary of Preliminary Clinical Results in Dogs

| Dog Type Ex. and Age | Diagnosis | Inhalation Treatment* | Time of Trial | Results |
|---|---|---|---|---|
| Breed 14 years old | metastasis (carcinoma) | CTX 25 mg), × 3 Dox 5 mg, × 1 | | PD visceral & Extra-pulmonary, died |
| 19 Flat-coated Retriever 8 years old | Excised salivary adeno-carcinoma, lung metastasis | Paclitaxel 22.5 mg, QW × 4 | 2-½ mo. | SD (4 weeks) lung PD lung, Rx discontinued |
| 20 Husky 16 years old | Advanced mammary adeno-carcinoma, lung metastasis | Paclitaxel 22.5 mg, × 2 (Paclitaxel 22.5 mg + Dox 5 mg), × 2 | 2 mo. | SD lung |

*Calculate target dose.
Abbreviations: PD = progressive disease, SD = stable disease; Dox =Doxorubicin; CTX = cyclophosphamide; QW = every week;

EXAMPLES 21 to 33

Additionally, tests were conducted in dogs using a defined protocol. In these tests, dogs with either gross metastatic disease, micrometastatic hemangiosarcoma or micrometastatic primary lung cancer were randomized to receive either doxorubicin, paclitaxel or both by inhalation via an endotracheal tube in a crossover design. Aerosol particle size was 2–3 μm as in the previous tests. The apparatus used was basically that shown in FIG. 5 and as described above. Formulations for administration of the drugs were as follows: 16 mg/ml doxorubicin in 70%ethanol/30%water; 75 mg paclitaxel in about 30% PEG/70%ethanol. Preferably the paclitaxel is administered with 0.2% of citric acid to prevent degradation of the drug unless it is immediately used after preparation. The treatments were administered once every two weeks, and if a diagnosis of progressive disease was made on two consecutive intervals the dog was crossed over to the alternate drug. At each treatment session, blood was sampled for hematology and biochemical analyses and urine was collected for analysis. The status of the tumors was monitored radiographically.

The results are summarized in Table 13. Pulmonary deposited doses listed in the table are based on scintigraphy studies that relate inhaled doses to deposited doses. Among the 10 dogs that had gross metastatic disease (Examples 21–28), which is regarded as a terminal condition with a very short life expectancy, 4 dogs (in Examples 21, 22, 24, and 27) showed stable disease in the lung indicating that the drug was having a positive effect. In the remaining 6 dogs (see Examples 23, 25, 26, and 28), the lung disease progressed. In two of the dogs with metastatic osteosarcoma (Examples 24 and 25) and in the dog with metastatic melanoma (Example 28), there were partial responses, i.e. there were tumors that decreased in size by more than 50%.

Four dogs had splenic hemangiosarcoma (Examples 29 and 30), a disease that invariably metastasizes to the lung and is fatal within two to four months. These dogs were given doxorubicin by inhalation in addition to intravenous chemotherapy to control systemic disease. The results in Table 13 show that each of the four dogs was alive (at least two months at the time of this writing) and that there was no evidence of disease in the lung.

The last group of dogs (Examples 31–33) are those that had primary lung tumors which were removed surgically. These dogs had metastases in their thoracic lymph nodes and have a life expectancy measured in weeks. As shown in Table 13, two dogs (Examples 31 and 32) received doxorubicin by inhalation (1.5 mg) and two dogs (Example 33) received paclitaxel (20 mg). The dog that received five treatments of doxorubicin was alive with no evidence of disease 81 days later suggesting that the treatment is having a positive effect. One dog (Example 32) received two doses of doxorubicin and died from metastases outside of the lung. The other two dogs (Example 33) have no evidence of disease but not enough time has passed to determine how effective the treatment will be.

The result of these tests, therefore, confirm those of the preliminary tests that inhalational chemotherapy is effective in the treatment of lung cancer.

TABLE 13

Efficacy of Inhalational Chemotherapy in Dogs with Lung Cancer

| Ex. | Diagnosis | No. of Dogs | Inhalation Treatment* | Results |
|---|---|---|---|---|
| 21 | Lung carcinoma | 1 | DOX 5 mg (5×) then paclitaxel 60 mg (2×) | SD |
| 22 | Metastatic hemangiosarcoma | 1 | DOX 5 mg (2×) | SD |
| 23 | Metastatic hemangiosarcoma | 1 | DOX 5 mg (1×) | PD |
| 24 | Metastatic osteosarcoma | 1 | DOX 5 mg (5×) + paclitaxel 60 mg (2×) | SD (PR after 3rd DOX treatment) |
| 25 | Metastatic osteosarcoma | 3 | DOX 5 mg (2×) + paclitaxel 60 mg (1×) | PD (PR in one dog) |
| 26 | Metastatic fibrosarcoma | 1 | DOX 5 mg (2×) | PD |
| 27 | Metastatic liposarcoma | 1 | DOX 5 mg (4×) + paclitaxel 60 mg (1×) | SD |
| 28 | Metastatic melanoma | 1 | paclitaxel 60 mg (2×) + DOX 5 mg (1×) | PD (PR noted in nodules < 2 cm) |
| 29 | Splenic hemangiosarcoma | 2 | DOX 5 mg (4×) + systemic chemotherapy | Alive and NED |
| 30 | Splenic hemangiosarcoma | 2 | DOX 1.5 mg (3×) + systemic chemotherapy | Alive and NED |
| 31 | Primary lung tumor | 1 | DOX 1.5 mg (5×) | Alive and NED |
| 32 | excised-micrometastatic disease | 1 | DOX 1.5 mg (2×) | Dead from extra-pleural metastases |
| 33 | | 2 | paclitaxel 20 mg (1×) | Alive and NED |

*Deposited pulmonary doses
DOX = doxorubicin; (×) = number of treatments received; SD = stable disease; PD = progressive disease; NED = no evidence of disease; PR = partial response (50% decrease in tumor size)

The safe and effective range of doses of the inhalant antineoplastic drugs in humans and animals (e.g. dogs and similar small animals) are shown in Table 14 below. Larger animal dosages can be calculated by using multiples of the small animal based dose based on the known relationship of (body weight in kg/m$^2$ of body surface area. The exact doses will vary depending upon such factors as the type and location of the tumor, the age and size of the patient, the physical condition of the patient and concomitant therapies that the patient may require. The dosages shown are for doses for one course of therapy. A course of therapy may be given, monthly, weekly, biweekly, triweekly or daily depending on the drug, patient, type of disease, stage of the disease and so on. Exemplary safe and effective amounts of carrier are given for each product have been published by the respective manufacturer and are summarized in the Physicians Desk Reference.

TABLE 14

| Drug | Animal Dose* mg/m² | Human Dose* mg/m² |
|---|---|---|
| Doxorubicin | 2 to 90 | 3 to 130 |
| Paclitaxel | 6 to 270 | 10 to 400 |
| Vincristine | 0.06 to 2 | 0.1 to 3 |
| Vinorelbine | 1.3 to 60 | 2 to 90 |
| Cisplatin | 4.6 to 200 | 7 to 300 |
| Etoposide | 4.6 to 200 | 7 to 300 |
| 9-Aminocampothecin | 2.6 to 10 | 0.04 to 15 |

*m² body surface area

Based on the results of the inhalation tests herein with doxorubicin, inhalation treatments with anthracyclines in addition to doxorubicin are also expected to be well tolerated and efficacious when administered by the pulmonary route. Based on the inhalation tests herein with vincristine and vinorelbine, other vinca alkaloids are expected to be well tolerated and efficacious when administered by the pulmonary route. Based on the inhalation tests herein for the vesicants doxorubicin, vincristine, vinorelbine, and paclitaxel, all of which are capable of serious vesicating injuries, other vesicating drugs (e.g. mechlorethamine, dactinomycin, mithramycin, bisantrene, amsacrine, epirubicin, daunorubicin, idarubicin, vinblastine, vindesine, and so on) are expected to be well tolerated and efficacious when administered by the pulmonary route. The exception, of course, would be vesicant drugs that are known to exhibit significant pulmonary toxicity when administered by IV (e.g. mitomycin-C). In this regard, a safe and effective amount of a particular drug or agent is that amount which based on its potency and toxicity, provides the appropriate efficacy/risk balance when administered via pulmonary means in the treatment of neoplasms. Similarly a safe and effective amount of a vehicle or carrier is that amount based on its solubility characteristics, stability, and aerosol forming characteristics, that provides the required amount of a drug to the appropriate site in the pulmonary system for treatment of the neoplasm.

For the nonvesicant antineoplastic drugs, based on the inhalation tests herein for the vesicating and nonvesicating drugs it is expected that all the nonvesicating drugs that do not exhibit direct pulmonary toxicity when administered intravenously are expected be well tolerated and exhibit efficacy. Bleomycin and mitomycin-C, for example, exhibit sufficient pulmonary toxicity to be excluded except when a chemoprotectant is used. In this regard typically carmustine, dacarbazine, melphalan, methotrexate, mercaptopurine, mitoxantrone, esorubicin, teniposide, aclacinomycin, plicamycin, streptozocin, menogaril are expected to be well tolerated and exhibit efficacy. Similarly, drugs of presently unknown classification such as geldanamycin, bryostatin, suramin, carboxyamido-triazoles such as those in U.S. Pat. No. 5,565,478, onconase, and SU101 and its active metabolite SU20 are likewise expected to be well tolerated and exhibit efficacy subject to the limitation on pulmonary toxicity. These drugs would be administered by the same methods disclosed for the tested antineoplastic drugs. They would be formulated with a safe and effective amount of a vehicle and administered in amounts and in a dosing schedule safe and effective for treating the neoplastic disease.

Pulmonary toxicity of compounds to be administered by inhalation is an important consideration. As mentioned above one of the major considerations is whether the drug exhibits significant pulmonary toxicity when injected by IV. While almost all antineoplastic drugs are toxic to the body and thus arguably exhibit pulmonary toxicity if given in a large enough dose, the test for pulmonary toxicity as used herein requires significant pulmonary toxicity at the highest manufacturers recommended dose that is to be administered to a patient. The determination of whether a drug exhibits sufficient pulmonary toxicity by IV so as to exclude it from the group of drugs useful for pulmonary administration can be made from the drug manufacturers recommendations as published in the Physicians Desk Reference (see "Physicians Desk Reference" 1997, (Medical Economics Co.), or later editions thereof), in other drug manuals published for health care providers, publicly available filings of the manufacturer with the FDA, or in literature distributed directly by the manufacturers to physicians, hospitals, and the like. For example in the "Physicians Desk Manual" 1997:

Doxorubicin (Astra) pp. 531–533—vesicant, there is no indication of pulmonary toxicity while cardiac toxicity, hematologic toxicity particularly leukopenia and myelosuppression; extravasation injuries are also noted;

Idarubicin (Pharmacia & Upjohn) pp 2096–2099—vesicant, primary toxicity appears to be myelosuppression no mention is made of pulmonary toxicity making the drug useful in the present invention;

Etoposide (Astra) pp539–541—no indication of pulmonary toxicity, but dose limiting hematologic toxicity is important;

Paclitaxel (Bristol-Meyers Squibb) pp. 723–727—vesicant, pulmonary toxicity is not listed for paclitaxel, but dose limiting bone marrow suppression (primarily neutropenia) is important;

Bleomycin (Blenoxane® Bristol-Meyers Squibb) pp. 697–699, pulmonary toxicities occur in about 10% of treated patients by IV administered drug, this makes bleomycin unacceptable for pulmonary administration for the present invention;

Mitomycin C (Mutamycin® Bristol-Meyers Squibb)— vesicant, infrequent but severe life threatening pulmonary toxicity has occurred by IV administration, this although infrequent severe life threatening pulmonary toxicity shows that the drug exhibits substantial pulmonary toxicity;

Methotrexate (Immunex) pp. 1322–1327—MW=454, primary toxicity appears to be hepatic and hematologic, signs of pulmonary toxicity should be closely monitored for signs of lesions;

Dactinomycin (Merck & Co.)—vesicant, primary toxicity appears to be oral, gastrointestinal, hematologic, and dermologic; no mention is made of pulmonary toxicity making the drug acceptable in the present invention;

mechlorethamine (Merck & Co.)—vesicant, primary toxicity appears to be renal, hepatic and bone marrow, no mention is made of pulmonary toxicity making the drug acceptable in the present invention;

Irinotecan (Camptosar® Pharmacia & Upjohn)—a derivative of camptothecin, primary toxicity appears to be severe diarrhea and neutropenia, no mention is made of pulmonary toxicity making the drug useful in the present invention;

Vincristine (Oncovin® Lilly) pp. 1521–1523—extremely toxic with high vesicant activity found in the tests herein, but no pulmonary toxicity noted;

Vinblastine (Velban® Lilly) pp.1537-1540—extremely toxic with high vesicant activity found in the tests herein, but no pulmonary toxicity noted.

The above listing is exemplary only and is not intended to limit the scope of the invention.

An additional embodiment of the invention includes methods and formulations that contain chemoprotectants and are administered by inhalation for preventing toxicity and particularly pulmonary toxicity that may be elicited by antineoplastic drugs. The method would allow the use by inhalation of antineoplastic drugs that exhibit pulmonary toxicity or would reduce the likelihood of pulmonary toxicity. One method would include treating a patient having a neoplasm, via inhalation administration, a pharmaceutically effective amount of a highly toxic antineoplastic drug and a pharmaceutically effective amount of a chemoprotectant, wherein the chemoprotectant reduces or eliminates toxic effects in the patient that are a result of inhaling the highly toxic antineoplastic drug. More narrowly, another embodiment includes a combination of inhaled chemoprotectant and antineoplastic drug that reduces or eliminates respiratory tract or pulmonary tract toxicity in the patient. The chemoprotectant can be coadministered with the antineoplastic drug by inhalation, or both by inhalation and by IV, or the chemoprotectant can be administered alone.

It is known, for example, that dexrazoxane (ICRF-187) when given by intraperitoneal injection to mice is protective against pulmonary damage induced by bleomycin given by subcutaneous injections. See for example Herman, Eugene et al, "Morphologic and morphometric evaluation of the effect of ICRF-187 on bleomycin-induced pulmonary toxicity", Toxicology 98, (1995) pp. 163–175, the text of which is incorporated by reference as if fully rewritten herein. The mice pretreated with intraperitoneal injections of dexrazoxane prior to having bleomycin injected subcutaneously showed reduced pulmonary alterations particularly fibrosis compared to another group of mice that was not pretreated.

The following examples illustrate the use of a chemoprotectant by inhalation in conjunction with an antineoplastic drug.

EXAMPLE 34

Dexrazoxane (ICRF-187) is dissolved in a pharmaceutically acceptable liquid formulation and administered to a patient as an aerosol using the apparatus and methods described herein, at a dose ranging from 10 mg to 1000 mg over a period of from one minute to one day prior to giving a chemotherapeutic drug such as doxorubicin by inhalation. The doxorubicin is given in a dose from 1 mg to 50 mg.

EXAMPLE 35

Dexrazoxane (ICRF-187) is administered as described in Example 34 at the same time or up to two hours before giving bleomycin by intravenous injection. The dose of dexrazoxane ranges form about 2 times to about 30 times the dose of bleomycin. The dose of bleomycin by IV ranges from about 5 to 40 units/m$^2$.

EXAMPLE 36

Dexrazoxane (ICRF-187) is administered as described in Example 34 at the same time or up to two hours before administering bleomycin by inhalation. The dose of dexrazoxane ranges from about 2 times to about 30 times the dose of bleomycin. The dose of bleomycin by inhalation ranges from 5 to 40 units/m$^2$ at intervals of from 1 week to 4 weeks.

EXAMPLES 37 and 38

Chemoprotectants such as mesna (ORG-2766), and ethiofos (WR2721) may be used in a manner similar to that described in Examples 34 to 36, above.

Combination Therapy

Another embodiment of the invention contemplates drug coadministration by the pulmonary route, and by (1) other local routes, and/or (2) systemically by IV. Results from the clinical tests on dogs indicates that, although the pulmonary route of administration will indeed control neoplastic cells arising in or metastatic to the pulmonary tract, neoplastic cells elsewhere in the body may continue to proliferate. This embodiment provides for effective doses of drug in the lung delivered via the lung and additional drug delivered via (1) other local sites (e.g. liver tumors may also be treated via hepatic artery instillation, ovarian cancer by intraperitoneal administration) and/or additional drug(s) may be provided systemically by IV via the general circulatory system. Administration can be at the same time, or administration followed closely in time by one or more of the other therapeutic routes. Benefits are that much higher dosages can be supplied to affected tissues and effective control of neoplasms can be maintained at multiple critical sites compared to using a single mode of administration.

Also contemplated within the scope of the invention is the combination of drugs for combination chemotherapy treatment. Benefits are those well known in the treatment of cancer using combination chemotherapy by other routes of administration. For example, combining drugs with different mechanisms of action such as an alkylating agent plus a mitotic poison plus a topoisomerase inhibitor. Such combinations increase the likelihood of destroying tumors that are comprised of cells with many different drug sensitivities. For example, some are easily killed by alkylating agents while mitotic poisons kill others more easily.

Also included in the invention are embodiments comprising the method for inhalation therapy disclosed herein and the application of radiotherapy, gene therapy, and/or immunotherapy. Other embodiments include the immediately above method combined with chemotherapy applied by IV and/or local therapy.

Also included within the invention are formulations for paclitaxel. In these formulations 100% to 40% ethanol is useful. However, to obtain better control of particle size and stable aerosol generation the addition of polyethylene glycol (PEG) is preferred. Although 1–60% PEG can be used about 8–40% PEG is more preferred, and 10-30% PEG was found to be optimal. A further embodiment also includes the addition of 0.01 to 2% of an organic or inorganic acid, preferably an organic acid such as citric acid and the like. The acid being added to stabilize the formulation. With regard to clinical use in inhalation, citric acid in water has been found to cause tussive and bronchioconstrictive effects. PEG may ameliorate this effect. The formulation contains a safe and effective amount of paclitaxel useful for the treatment of neoplasms.

While the forms of the invention herein disclosed constitute presently preferred embodiments, many others are possible. It is not intended herein to mention all of the possible equivalent forms or ramifications of the invention. It is to be understood that the terms used herein are merely descriptive, rather than limiting, and that various changes may be made without departing from the spirit of the scope of the invention.

We claim:

1. A method of treating cancer of the respiratory tract in a patient in need of treatment which comprises administering by inhalation a pharmaceutically safe and effective amount of a vesicant anthracycline anti-cancer agent, wherein said anti-cancer agent is unencapsulated.

2. A method according to claim 1 wherein said anthracycline anti-cancer agent is selected from the group consisting of doxorubicin, epirubicin, daunorubicin, cyanomorpylinyl-doxorubicin and idarubicin.

3. A method according to claim 2 wherein said anthracycline anti-cancer agent is selected from the group consisting of doxorubicin and epirubicin and idarubicin.

4. A method according to claim 1 wherein said anthracycline anti-cancer agent is doxorubicin.

5. A method according to claim 1 wherein said anthracycline anti-cancer agent is epirubicin.

6. A method according to claim 1 wherein said anthracycline anti-cancer agent is idarubicin.

7. A method according to claim 1 wherein said anthracycline anti-cancer agent is administered by inhalation as an aerosolized liquid, powder or gas.

8. A method according to claim 7 wherein said aerosolized anthracycline is administered as an aerosolized liquid.

9. A method according to claim 7 wherein said aerosolized anthracycline is administered as an aerosolized powder.

10. A method according to claim 7 wherein said anthracycline is doxorubicin, epirubicin or idarubicin.

11. A method according to claim 7 wherein said anthracycline anti-cancer agent is administered as an aerosolized liquid at a dosage of from about 3 mg/m$^2$ body surface area to about 130 mg/m$^2$ body surface area.

12. A method according to claim 7 wherein said anthracycline anti-cancer agent is administered as an aerosolized powder at a dosage of from about 3 mg/m$^2$ body surface area to about 130 mg/m$^2$ body surface area.

13. A method according to claim 1 wherein said anthracycline anti-cancer agent is administered at a dosage of from about 3 mg/m$^2$ body surface area to about 130 mg/m$^2$ body surface area.

14. A method according to claim 1 wherein the particle size of said aerosol is from about 0.1 μm to about 10.0 μm.

15. A method according to claim 14 wherein the particle size of said aerosol is from about 1.0 μm to about 5.0 μm.

16. A method according to claim 15 wherein the particle size of said aerosol is from about 2.0 μm to about 2.5 μm.

17. A method according to claim 1 wherein one or more non-anthracycline vesicant anti-cancer agents are administered by inhalation at the same time as the anthracycline anticancer agent.

18. A method of treating cancer of the respiratory tract in a patient which comprises administering to said patient a pharmaceutically safe and effective amount of an aerosolized active drug substance which is an anthracycline anti-cancer agent; wherein said anthracycline anti-cancer agent is administered at a dosage of from about 3 mg/m$^2$ body surface to about 130 mg/m$^2$ body surface area; wherein said active drug substance is delivered to said patient using a means for aerosolization of said active drug substance; and wherein the particle size of said aerosolized drug substance is from about 0.1 μm.

19. A method according to claim 18 wherein said anthracycline anti-cancer agent is selected from the group consisting of doxorubicin, epirubicin, and idarubicin.

20. A method according to claim 19 wherein said anthracycline anti-cancer agent is doxorubicin.

21. A method according to claim 19 wherein said anthracycline anti-cancer agent is epirubicin.

22. A method according to either of claim 18 wherein said anthracycline anti-cancer agent is administered as an aerosolized liquid or powder.

23. A method according to claim 22 wherein said anthracycline anti-cancer agent is doxorubicin or epirubicin and is administered as an aerosolized liquid.

24. A method according to claim 22 wherein said anthracycline anti-cancer agent is doxorubicin or epirubicin and is administered as an aerosolized powder.

* * * * *